(12) United States Patent
Pu et al.

(10) Patent No.: US 11,471,940 B2
(45) Date of Patent: Oct. 18, 2022

(54) METHODS OF PRODUCING COBALT NANOPARTICLES AND HOLLOW GOLD NANOSPHERES AND KITS FOR PRACTICING SAME

(71) Applicant: The Regents of the University of California, Oakland, CA (US)

(72) Inventors: Ying-Chih Pu, Santa Cruz, CA (US); Frank Song, Santa Cruz, CA (US); Weichun Zhang, Santa Cruz, CA (US); Sarah Lindley, Santa Cruz, CA (US); Staci Adams, Santa Cruz, CA (US); Jin Zhang, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 273 days.

(21) Appl. No.: 16/465,708

(22) PCT Filed: Dec. 1, 2017

(86) PCT No.: PCT/US2017/064334
§ 371 (c)(1),
(2) Date: May 31, 2019

(87) PCT Pub. No.: WO2018/102765
PCT Pub. Date: Jun. 7, 2018

(65) Prior Publication Data
US 2020/0114420 A1   Apr. 16, 2020

Related U.S. Application Data

(60) Provisional application No. 62/428,933, filed on Dec. 1, 2016.

(51) Int. Cl.
*B22F 9/24* (2006.01)
*B22F 1/054* (2022.01)
*A61N 5/06* (2006.01)

(52) U.S. Cl.
CPC ............... *B22F 1/054* (2022.01); *B22F 9/24* (2013.01); *A61N 5/062* (2013.01); *B22F 1/0549* (2022.01);
(Continued)

(58) Field of Classification Search
None
See application file for complete search history.

(56) References Cited

U.S. PATENT DOCUMENTS

2009/0263485 A1   10/2009  Li et al.
2011/0318415 A1*  12/2011  Li ..................... A61K 31/704
                                                            424/486
(Continued)

OTHER PUBLICATIONS

Jiang, X.C. et al., "Role of Temperature in the Growth of Silver Nanoparticles Through a Synergetic Reduction Approach", Nanoscale Research Letters, 6:32, 2011, Published Sep. 23, 2010.*
(Continued)

*Primary Examiner* — George Wyszomierski
(74) *Attorney, Agent, or Firm* — Brian E. Davy; Bozicevic, Field & Francis LLP

(57) ABSTRACT

Provided are methods of producing cobalt nanoparticles (Co NPs). The methods include combining a cobalt salt, a capping agent, and a reducing agent, under Co NP synthesis conditions including a temperature selected to produce cobalt nanoparticles of a pre-selected diameter, where the temperature and pre-selected diameter are inversely related. In certain aspects, the methods further include producing hollow gold nano spheres (HGNs) using the cobalt nanoparticles as scaffolds. Also provided are cobalt nanoparticles and hollow gold nano spheres (HGNs) produced according to the present methods. Kits that find use in practicing the methods of the present disclosure are also provided.

12 Claims, 10 Drawing Sheets

(52) U.S. Cl.
CPC ..... *B22F 2301/15* (2013.01); *B22F 2301/255* (2013.01)

(56) References Cited

U.S. PATENT DOCUMENTS

| | | |
|---|---|---|
| 2012/0045754 A1 | 2/2012 | Zhang et al. |
| 2012/0057165 A1* | 3/2012 | Natan ............... G01N 33/532 356/445 |
| 2014/0012224 A1 | 1/2014 | Zhang et al. |
| 2014/0024026 A1 | 1/2014 | Alocilja et al. |

OTHER PUBLICATIONS

Gomez et at. (2014) "Scaled-up production of plasmonic nanoparticles using microfluidics: from metal precursors to functionalized and sterilized nanoparticles" Lab on a Chip, 14:325-332.

Liang et al. (2005) "Gold hollow nanospheres: tunable surface plasmon resonance controlled by interior-cavity sizes" J. Phys. Chem. B., 109:7795-7800.

Liu et al. (2015) "Anti-EGFR-Conjugated Hollow Gold Nanospheres Enhance Radiocytotoxic Targeting of Cervical Cancer at Megavoltage Radiation Energies" Nanoscale Res. Lett., 10:218.

Lu et al. (2009) "Targeted Photothermal Ablation of Murine Melanomas with Melanocyte-Stimulating Hormone Analog-Conjugated Hollow Gold Nanospheres" Clin. Cancer Res., 15:876-886.

Melancon et al. (2008) "In vitro and in vivo targeting of hollow gold nanoshells directed at epidermal growth factor receptor for photothermal ablation therapy" Mol. Cancer Ther., 7:1730-1739.

Schwartzberg et al. (2006) "Synthesis, Characterization, and Tunable Optical Properties of Hollow Gold Nanospheres" Journal of Physical Chemistry B, 110(4): 19935-19944.

\* cited by examiner

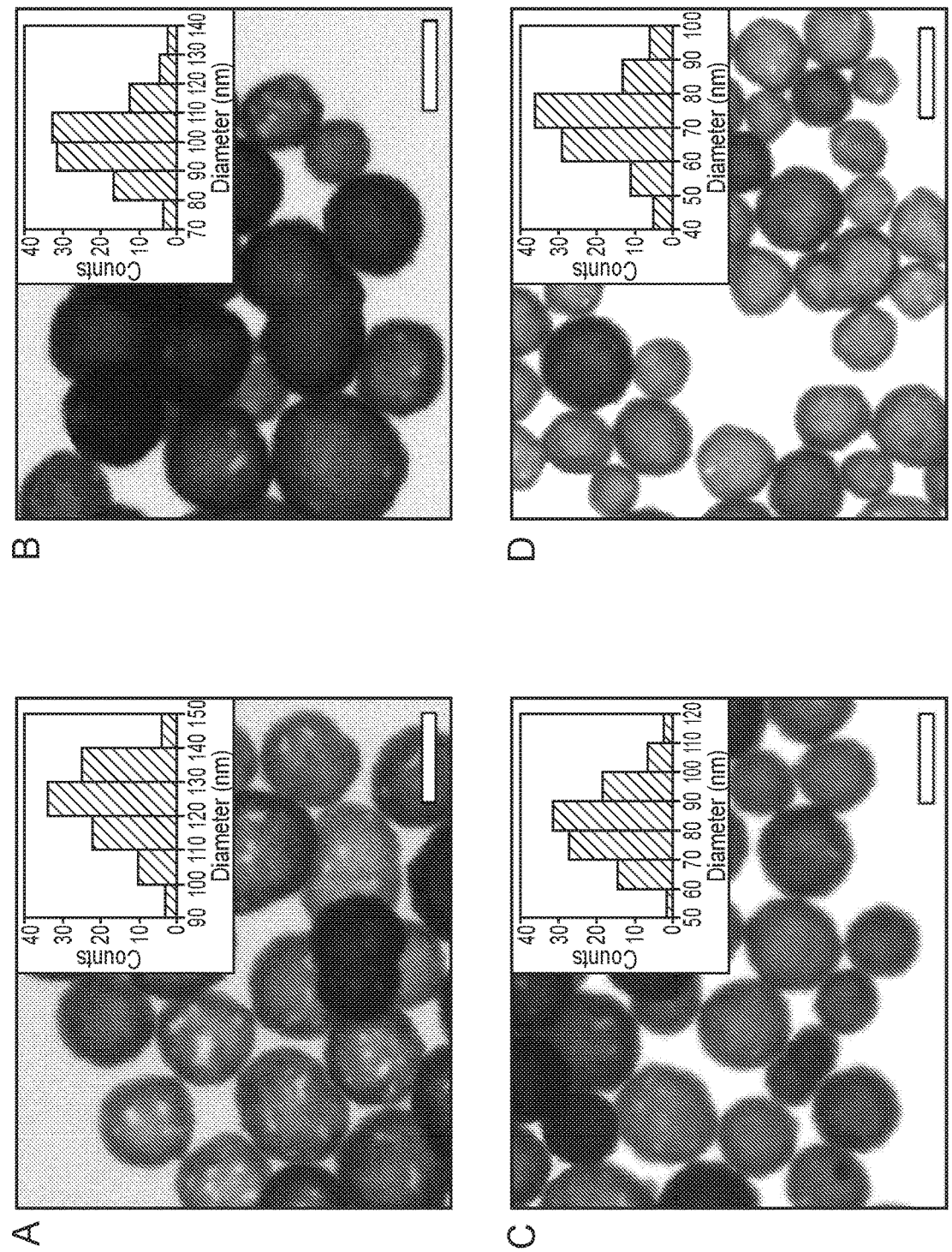

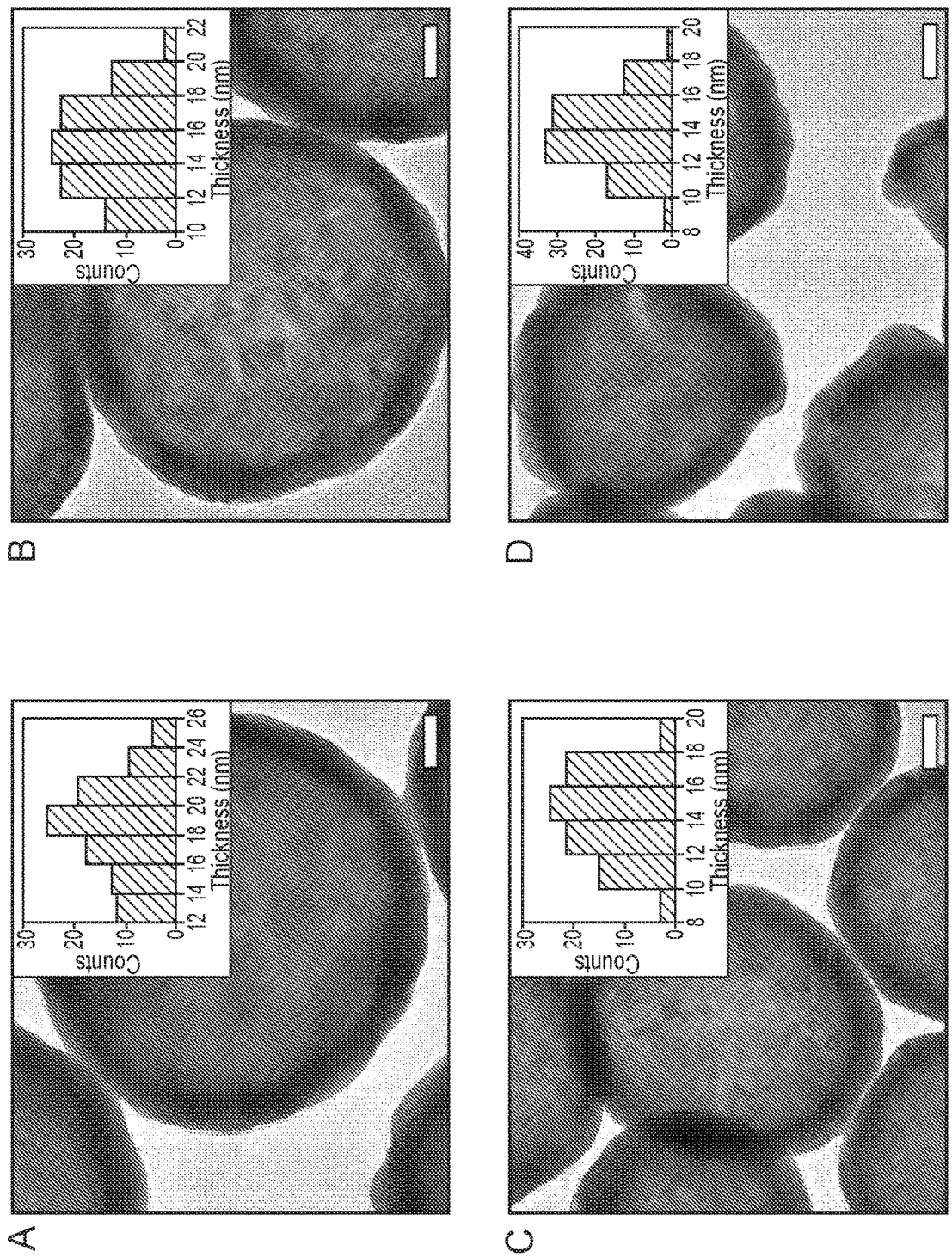

US 11,471,940 B2

METHODS OF PRODUCING COBALT NANOPARTICLES AND HOLLOW GOLD NANOSPHERES AND KITS FOR PRACTICING SAME

CROSS-REFERENCE TO RELATED APPLICATIONS

This application claims the benefit of U.S. Provisional Patent Application No. 62/428,933, filed Dec. 1, 2016, which application is incorporated herein by reference in its entirety.

STATEMENT REGARDING FEDERALLY SPONSORED RESEARCH

This invention was made with Government support under contract number NNX15AQ01A awarded by the National Aeronautics and Space Administration, and contract number DE-AC02-05CH11231 awarded by the U.S. Department of Energy. The Government has certain rights in the invention.

INTRODUCTION

Noble metal nanostructures have been studied extensively because of their unique surface plasmon resonance (SPR) due to the collective oscillation of conductive band electrons induced by interaction with a resonant wavelength of light. This property is tunable through control of their shape and size.[1-4] These nanoparticles find use in many applications including surface-enhanced Raman scattering (SERS),[5-6] photothermal therapy (PTT),[7-8] plasmonic enhanced photoelectric conversion, chemical catalysis[9] and biosensors.[10-15] Since many of these applications require specific absorption and/or scattering properties, the ability to tune the SPR absorption and scattering is highly desirable. For example, while PTT benefits from enhanced absorption in the near infrared (NIR) for deeper tissue penetration, SERS requires both strong absorption and scattering.[16-17][18-19] In order to meet the different optical requirements for each application, a variety of metal nanostructures have been developed in recent years with the goal to control their optical properties. These include spherical nanoparticles (NPs),[20-21] nanorods,[22-23] nanocages,[24-25] nanoshells,[26-28] nanostars[29] and nanoprisms.[30-31]

A promising metal nanostructure is the hollow gold nanosphere (HGN), which exhibits a tunable SPR across the visible region and out to the NIR. The optical properties for HGNs can be tuned by adjusting the ratio between particle size and shell thickness.[32-33] These nanoparticles have performed strongly in both PTT, drug delivery, and imaging.[34-36]

To date, a significant amount of work has been carried out on the synthesis of HGNs with many attempts to develop methods for controlling structural and optical properties of HGNs.[32, 37-40] The most popular approach to HGN synthesis follows the scheme shown in FIG. 1. A sacrificial cobalt scaffold is initially formed as $Co^{2+}$ reduced by $NaBH_4$. As the cobalt scaffold is exposed to air, oxidation occurs while, a Au shell is deposited on the cobalt scaffold through galvanic exchange.[41-42] Further oxidation of the cobalt scaffold results in a hollow structure comprising a gold shell and a solvent-filled dielectric core. The structural dimension and SPR of the resulting HGN are controlled by the cobalt scaffold. Tuning the SPR of the resulting HGN can be done by altering the size of the initial cobalt scaffold.

Initially, Liang and co-workers demonstrated a uniform HGN synthesis with tunable interior-cavity sizes by controlling the size of the cobalt nanoparticle (Co NP) scaffold using different stoichiometric ratios of $HAuCl_4$ and $NaBH_4$.[43] In addition, the synthesis of HGNs with tunable size and SPR can be achieved by controlling the ratio of the HGN outer diameter and the shell thickness.[32] This aspect ratio was achieved by varying the concentration of the Co NP precursors including the cobalt salt, sodium citrate (capping agent), and sodium borohydride (reducing agent). In addition, the mixing rate of the precursors also influenced the particle size distribution of the cobalt scaffold. The size of the cobalt scaffold and therefore the dimensions of HGN could be altered by changing the concentration and processing of the initial precursors.[32] However, a convenient method for producing HGNs with tunable size and SPR is still needed for practical utilization of HGNs in different applications.

SUMMARY

Provided are methods of producing cobalt nanoparticles (Co NPs). The methods include combining a cobalt salt, a capping agent, and a reducing agent, under Co NP synthesis conditions including a temperature selected to produce cobalt nanoparticles of a pre-selected diameter, where the temperature and pre-selected diameter are inversely related. In certain aspects, the methods further include producing hollow gold nanospheres (HGNs) using the cobalt nanoparticles as scaffolds. Also provided are cobalt nanoparticles and hollow gold nanospheres (HGNs) produced according to the present methods. Kits that find use in practicing the methods of the present disclosure are also provided.

BRIEF DESCRIPTION OF THE FIGURES

Some of the figures are better understood when provided in color. Applicant submits that the color versions of the figures are part of the original disclosure and reserves the right to provide color versions of the figures in later proceedings.

DETAILED DESCRIPTION

Figure 1:
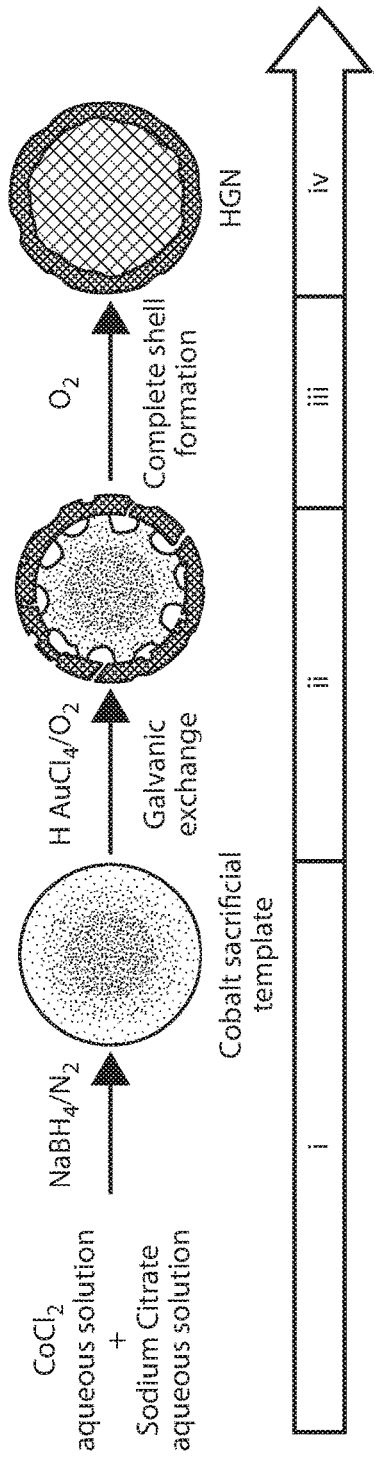
FIG. 1 is a schematic illustration of a method of producing cobalt nanoparticles (Co NPs) and, subsequently therefrom, hollow gold nanospheres (HGNs), according to one embodiment of the present disclosure. i. Cobalt NP scaffold formation; ii. Au shell deposition via galvanic exchange; iii. Oxidation of cobalt scaffold; and iv. Complete Au shell formation.

Provided are methods of producing cobalt nanoparticles (Co NPs). The methods include combining a cobalt salt, a capping agent, and a reducing agent, under Co NP synthesis conditions including a temperature selected to produce cobalt nanoparticles of a pre-selected diameter, where the temperature and pre-selected diameter are inversely related. In certain aspects, the methods further include producing hollow gold nanospheres (HGNs) using the cobalt nanoparticles as scaffolds. Also provided are cobalt nanoparticles and hollow gold nanospheres (HGNs) produced according to the present methods. Kits that find use in practicing the methods of the present disclosure are also provided.

Before the methods, kits, and compositions of the present disclosure are described in greater detail, it is to be understood that the methods, kits, and compositions are not limited to particular embodiments described, as such may, of course, vary. It is also to be understood that the terminology used herein is for the purpose of describing particular embodiments only, and is not intended to be limiting, since the scope of the methods, kits, and compositions will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, kits, and compositions. The upper and lower limits of these smaller ranges may independently be included in the smaller ranges and are also encompassed within the methods, kits, and compositions, subject to any specifically excluded limit in the stated range. Where the stated range includes one or both of the limits, ranges excluding either or both of those included limits are also included in the methods, kits, and compositions.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, kits, and compositions belong. Although any methods, kits, and compositions similar or equivalent to those described herein can also be used in the practice or testing of the methods, kits, and compositions, representative illustrative methods, kits, and compositions are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, kits, and compositions are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, kits, and compositions, which are, for clarity, described in the context of separate embodiments, may also be provided in combination in a single embodiment. Conversely, various features of the methods, kits, and compositions, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods, kits, and compositions and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods, kits, and compositions. Any recited method can be carried out in the order of events recited or in any other order that is logically possible.

Methods

As summarized above, provided by the present disclosure are methods of producing cobalt nanoparticles (abbreviated herein as "Co NPs"). In some embodiments, the methods are for producing cobalt nanoparticles of a pre-selected diameter, such methods including combining a cobalt salt, a capping agent, and a reducing agent, under Co NP synthesis conditions including a temperature selected to produce cobalt nanoparticles of a pre-selected diameter, where the temperature and pre-selected diameter are inversely related.

By "pre-selected diameter" is meant a pre-selected average diameter of the population of Co NPs produced under the Co NP synthesis conditions. By "pre-selected" is meant the practitioner of the subject methods selects a desired average diameter of the Co NPs prior to production of the Co NPs, where the desired average diameter of the Co NPs is achieved by selecting a temperature or profile thereof during Co NP synthesis that determines the resulting average diameter of the Co NPs. The temperature and pre-selected diameter are inversely related. Unless specified otherwise, the diameter of an individual Co NP is the largest linear dimension of the individual Co NP (rather than the hydrodynamic diameter of the individual Co NP), and the average diameter of a population of Co NPs is the average of the largest linear dimension of Co NPs of the population (rather than the average hydrodynamic diameter of Co NPs of the population).

The methods of the present disclosure are based in part on the inventors' unexpected findings that the size of Co NPs may be "tuned" based on a single parameter—the temperature or profile thereof during Co NP synthesis, where synthesis at lower temperatures produces Co NPs having a larger average diameter and synthesis at higher temperatures produces Co NPs having a smaller average diameter. Based on the detailed guidance provided by the present disclosure, one may produce Co NPs of a pre-selected diameter by selecting a corresponding temperature during Co NP synthesis.

In certain aspects, the pre-selected diameter of the Co NPs ranges from about 10 to about 200 nm, e.g., from about 30 to about 150 nm. For example, the pre-selected diameter of the Co NPs may be about 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, or about 200 nm. In some embodiments, the pre-selected diameter of the Co NPs ranges from about 10 to about 200 nm, 10 to 190 nm, 10 to 180 nm, 10 to 170 nm, 10 to 160 nm, 10 to 150 nm, 10 to 140 nm, 10 to 130 nm, 10 to 120 nm, 10 to 110 nm, 10 to 100 nm, 10 to 90 nm, 10 to 80 nm, 10 to 70 nm, 10 to 60 nm, 10 to 50 nm, 10 to 40 nm, 10 to 30 nm, or from about 10 to about 20 nm. In certain aspects, the pre-selected diameter of the Co NPs ranges from about 10 to about 200 nm, 20 to 200 nm, 30 to 200 nm, 40 to 200 nm, 50 to 200 nm, 60 to 200 nm, 70 to 200 nm, 80 to 200 nm, 90 to 200 nm, 100 to 200 nm, 110 to 200 nm, 120 to 200 nm, 130 to 200 nm, 140 to 200 nm, 150 to 200 nm, 160 to 200 nm, 170 to 200 nm, 180 to 200 nm, or from about 190 to about 200 nm. In some embodiments, the pre-selected diameter of the Co NPs ranges from about 10 to about 20 nm, 20 to 30 nm, 30 to 40 nm, 40 to 50 nm, 50 to 60 nm, 60 to 70 nm, 70 to 80 nm, 80 to 90 nm, 90 to 100 nm, 100 to 110 nm, 110 to 120 nm, 120 to 130 nm, 130 to 140 nm, 140 to 150 nm, 150 to 160 nm, 160 to 170 nm, 170 to 180 nm, 180 to 190 nm, or from about 190 to about 200 nm. In some embodiments, the pre-selected diameter of the Co NPs ranges from about 10 to about 20 nm, 20 to 30 nm, 30 to 40 nm, 40 to 50 nm, 50 to 60 nm, 60 to 70 nm, 70 to 80 nm, 80 to 90 nm, 90 to 100 nm, 110 to 120 nm, 120 to 130 nm, 130 to 140 nm, 140 to 150 nm, 150 to 160 nm, 160 to 170 nm, 170 to 180 nm, 180 to 190 nm, or from about 190 to about 200 nm.

In certain aspects, the pre-selected diameter of the Co NPs ranges from about 30 to about 230 nm, from 40 to 220 nm, from 50 to 210 nm, from 60 to 200 nm, from 70 to 190 nm, from 80 to 180 nm, from 90 to 170 nm, from 100 to 160 nm, from 110 to 150 nm, or from 120 to 140 nm. In some embodiments, the pre-selected diameter of the Co NPs ranges from about 110 nm to about 150 nm, e.g., about 115 nm to about 145 nm. In certain aspects, the pre-selected diameter of the Co NPs is 10 nm or more, 20 nm or more, 30 nm or more, 40 nm or more, 50 nm or more, 60 nm or more, 70 nm or more, 80 nm or more, 90 nm or more, 100 nm or more, 110 nm or more, 120 nm or more, 130 nm or more, 140 nm or more, 150 nm or more, 160 nm or more, 170 nm or more, 180 nm or more, 190 nm or more, or 200 nm or more. In some embodiments, the pre-selected diameter of the Co NPs is 200 nm or less, 190 nm or less, 180 nm or less, 170 nm or less, 160 nm or less, 150 nm or less, 140 nm or less, 130 nm or less, 120 nm or less, 110 nm or less, 100 nm or less, 90 nm or less, 80 nm or less, 70 nm or less, 60 nm or less, 50 nm or less, 40 nm or less, 30 nm or less, 20 nm or less, or 10 nm or less.

As will be appreciated, the diameters of individual Co NPs produced according to subject methods will vary around the pre-selected diameter. In some embodiments, the diameters of the Co NPs produced will vary around the pre-selected diameter (e.g., any of the pre-selected diameters provided in the preceding paragraph) by 20% or less, 17.5% or less, 15% or less, 12.5% or less, 10% or less, 7.5% or less, 5% or less, or 2.5% or less.

The pre-selected diameter of the Co NPs produced according to the methods of the present disclosure may be readily confirmed using any suitable approach. For example, the pre-selected diameter may be confirmed using approaches such as transmission-mode scanning electron microscopy (tSEM, e.g., using an FEI Quanta 3D Dual beam SEM), high-resolution transmission electron microscopy (HRTEM, e.g., using an FEI UT Tecnai HRTEM microscope operated at 200 kV accelerating voltage), non-limiting examples of which are described in the Experimental section below.

As summarized above, the methods include combining the cobalt salt, capping agent and reducing agent under Co NP synthesis conditions that include a temperature selected to produce cobalt nanoparticles having the pre-selected diameter. As will be appreciated based on the teachings of the present disclosure, the temperature is selected based on the pre-selected diameter, where synthesis at lower temperatures produces Co NPs having a larger average diameter and synthesis at higher temperatures produces Co NPs having a smaller average diameter. In certain aspects, the selected temperature ranges from about 5° C. to about 90° C. For example, the selected temperature may range from about 10° C. to about 80° C. In some embodiments, the selected temperature ranges from about 10° C. to about 80° C., 20° C. to 80° C., 30° C. to 80° C., 40° C. to 80° C., 50° C. to 80° C., 60° C. to 80° C., or about 70° C. to about 80° C. In certain aspects, the selected temperature ranges from about 10° C. to about 80° C., 10° C. to 70° C., 10° C. to 60° C., 10° C. to 50° C., 10° C. to 40° C., 10° C. to 30° C., or about 10° C. to about 20° C. In some embodiments, the selected temperature ranges from about 10° C. to about 20° C., 20° C. to 30° C., 30° C. to 40° C., 40° C. to 50° C., 50° C. to 60° C., 60° C. to 70° C., 70° C. to 80° C., or 80° C. to 90° C. In certain aspects, the selected temperature ranges from about 5° C. to about 30° C., including from about 7.5° C. to about 25° C., e.g., from about 10° C. to about 20° C. The selected temperature may be provided using any suitable device or method.

For example, synthesis may occur by combining the cobalt salt, capping agent, reducing agent, and any other reagents useful for Co NP synthesis into a reaction mixture within a suitable vessel (e.g., tube, vial, flask, plate (e.g., 96-well or other plate), or the like) placed in an environment (e.g., temperature-controlled environment) that brings the reaction mixture to the selected temperature. Suitable environments include a water bath (e.g., a heated water bath, a cooled water bath (e.g., a water bath cooled with ice), or the like), a heat block, a cooling block, an incubator, a thermocycler, or the like. In some embodiments, the environment is programmable to subject the reaction mixture to a constant temperature during Co NP synthesis or a temperature profile that includes two or more temperatures during Co NP synthesis.

As described in the Experimental section herein, the inventors have determined that Co NPs of 145.0±18.5, 115.4±16.7, 101.7±10.6, 87.3±10.1, 75.8±6.8, 66.2±6.3, 45.8±5.7 and 33.6±4.5 nm may be produced by employing selected temperatures of 10, 20, 30, 40, 50, 60, 70, and 80° C., respectively, using the example cobalt salt, capping agent, reducing agent, and concentrations thereof described therein.

In some embodiments, the Co NP synthesis conditions include a constant temperature (e.g., any of the temperatures provided in the preceding paragraph)—that is, a selected temperature that remains constant during Co NP synthesis, where the selected constant temperature determines the average diameter of the Co NPs produced. In other embodiments, the Co NP synthesis conditions include a temperature profile such that the Co NP synthesis conditions include two or more selected temperatures during Co NP synthesis (e.g., two or more of any of the selected temperatures described above), where the two or more selected temperatures determine the average diameter of the Co NPs produced.

The cobalt salt may be any cobalt salt suitable for synthesis of cobalt nanoparticles, which salt may be selected based on the type of capping agent, reducing agent, and/or any other reagents employed for Co NP synthesis. In some embodiments, the cobalt salt is an anhydrous cobalt salt. A non-limiting example of an anhydrous cobalt salt that may be employed when practicing the subject methods is $CoCl_2$. Other suitable cobalt salts include, but are not limited to, $CoBr_2$, $CoI_2$, $Co(NO_3)_2$, $Co(acac)_2$, Cobalt(II) acetate, etc.

The capping agent may be any capping agent suitable for synthesis of cobalt nanoparticles, which capping agent may be selected based on the type of cobalt salt, reducing agent, and/or any other reagents employed for Co NP synthesis. In some embodiments, the capping agent is a sodium salt of citrate. A non-limiting example of a capping agent that is a sodium salt of citrate is trisodium citrate. Other suitable capping agents include, but are not limited to, polyvinylpyrrolidone (PVP), polyethylene glycol (PEG), polyvinyl alcohol (PVA), polyethyleneimine (PEI), cetyltrimethyl ammonium bromide (CTA-Br), cetyltrimethyl ammonium chloride (CTA-Cl), etc.

The reducing agent may be any reducing agent suitable for synthesis of cobalt nanoparticles, which reducing agent may be selected based on the type of cobalt salt, capping agent, and/or any other reagents employed for Co NP synthesis. In some embodiments, the reducing agent is a salt comprising boron. A non-limiting example of a reducing agent that is a salt comprising boron is a salt comprising a tetrahedral $BH_4^-$ anion. In one such example, the reducing agent is $NaBH_4$. Other suitable reducing agents include, but are not limited to, citrate-Na, ascorbic acid, formaldehyde, etc.

In some embodiments, the methods include iteratively producing cobalt nanoparticles having different pre-selected diameters such that the pre-selected diameter of one iteration is different from the pre-selected diameter of a second iteration, and where the different pre-selected diameters are achieved by (e.g., solely by) Co NP synthesis conditions including different selected temperatures. By "iteratively" is meant two or more separate Co NP synthesis reactions performed successively, in parallel, or a combination thereof. For example, in certain aspects, provided is a method that further includes producing cobalt nanoparticles of a different pre-selected diameter by combining a cobalt salt, a capping agent, and a reducing agent, under Co NP synthesis conditions comprising a different temperature selected to produce cobalt nanoparticles of the different pre-selected diameter, wherein the different temperature and different pre-selected diameter are inversely related. By "different" pre-selected diameter and "different" temperature is meant that the pre-selected diameter and corresponding selected temperature are different from those of a second Co NP synthesis reaction, which second Co NP synthesis reaction may occur prior to, in parallel with, or subsequent to the Co NP synthesis reaction having the different pre-selected diameter and different corresponding selected temperature. In certain aspects, different iterations of the Co NP synthesis reactions employ the same cobalt salt, capping agent, reducing agent, and concentrations thereof. In some embodiments, the only difference or only substantial difference between the Co NP synthesis conditions of a first Co NP synthesis reaction for producing Co NPs of a first selected diameter and a second Co NP synthesis reaction for producing Co NPs of a second selected diameter is the selected temperature or profile thereof at which the synthesis reactions occur.

In certain aspects, the Co NP synthesis conditions are air-free or substantially air-free. Such conditions are useful for preventing oxidation, aggregation, or both. For example, a vacuum gas manifold (e.g., a Schlenk line) may be employed to remove air (e.g., replace air with $N_2$ gas) from the vessel in which the synthesis reaction will take place. In one embodiment, the cobalt salt and capping agent are added to the reaction vessel, air is removed from the reaction vessel (e.g., by replacement of the air with $N_2$ gas using a Schlenk line), and subsequent to removal of the air, the reducing agent is added to commence the synthesis reaction under air-free conditions.

Also provided are Co NPs produced according to any of the methods of the present disclosure. The Co NPs may be present in a container, such as a vial, tube, plate (e.g., 96-well or other plate), flask, or the like. In some embodiments, the Co NPs are present in a liquid medium, e.g., water or other suitable liquid storage medium.

Any of the methods described above may further include, subsequent to producing the cobalt nanoparticles, producing hollow gold nanospheres (HGNs) using the cobalt nanoparticles as scaffolds. HGNs have hollow solvent-filled dielectric cores and polycrystalline gold shells that, due to the two surfaces or interfaces, can generate enhanced electromagnetic (EM) fields. Any suitable approach may be employed to produce HGNs from the Co NPs. In one embodiment, HGNs are produced from the Co NP scaffolds via a galvanic exchange reaction. In one non-limiting example, a suitable galvanic exchange reagent (e.g., $HAuCl_4$) may be combined with a solution containing the Co NPs (e.g., the Co NP synthesis reaction mixture) under air atmosphere and swirled (e.g., by hand, using a laboratory shaker, or the like) to effect galvanic exchange, oxidation of the Co NPs, and completion of shell formation. Details regarding this example approach may be found, e.g., in Liang et al. (2005) *J. Phys. Chem. B*. 109:7795. A flow diagram illustrating the example method of producing HGNs from Co NP scaffolds by galvanic exchange is provided in FIG. 1, and experimental details for this example approach are provided in the Experimental section below.

As demonstrated in the Experimental section below, HGNs produced from the Co NP scaffolds will have a diameter primarily determined by the pre-selected diameter of the Co NPs. In this way, the present disclosure provides the size-tunable synthesis of HGNs by controlling the temperature at which Co NP synthesis occurs. In other words, the HGN diameter may be pre-selected based on the pre-selected diameter of the Co NPs achieved by appropriate temperature selection during Co NP synthesis. Accordingly, in some embodiments, the methods of the present disclosure are methods of tuning HGNs to have a particular property (e.g., spectral property, photothermal property, and/or the like) where the property is based at least in part on the average diameters of the HGNs as determined by the pre-selected diameter of the Co NPs, which pre-selected diameter is achieved by the selected temperature (e.g., solely by the selected temperature) at which Co NP synthesis occurs. Unless specified otherwise, the diameter of an individual HGN is the largest linear dimension of the individual HGN (rather than the hydrodynamic diameter of the individual HGN), and the average diameter of a population of HGNs is the average of the largest linear dimension of HGNs of the population (rather than the average hydrodynamic diameter of HGNs of the population).

In some embodiments, HGNs produced in accordance with the methods of the present disclosure have an average diameter of from about 10 to about 200 nm (e.g., from about 20 to about 150 nm), where the average HGN diameter is determined by the pre-selected diameter of the Co NPs. For example, the average HGN diameter may be about 10 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 170 nm, 180 nm, 190 nm, or about 200 nm. In some embodiments, the average HGN diameter ranges from about 10 to about 20 nm, 20 to 30 nm, 30 to 40 nm, 40 to 50 nm, 50 to 60 nm, 60 to 70 nm, 70 to 80 nm, 80 to 90 nm, 90 to 100 nm, 100 to 105 nm, 105 to 110 nm, 110 to 115 nm, 115 to 120 nm, 120 to 125 nm, 125 to 130 nm, 130 to 135 nm, 135 to 140 nm, 140 to 145 nm, 145 to 150 nm, 150 to 155 nm, 155 to 160 nm, 160 to 165 nm, 165 to 170 nm, 170 to 175 nm, 175 to 180 nm, 180 to 185 nm, 185 to 190 nm, 190 to 195 nm, or about 195 to about 200 nm. In certain aspects, the average HGN diameter is from about 50 to about 170 nm, from 60 to 160 nm, from 70 to 150 nm, from 80 to 140 nm, from 90 to 130 nm, or from about 100 to about 120 nm. In some embodiments, the average HGN diameter is 10 nm or more, 20 nm or more, 30 nm or more, 40 nm or more, 50 nm or more, 60 nm or more, 70 nm or more, 80 nm or more, 90 nm or more, 100 nm or more, 110 nm or more, 120 nm or more, 130 nm or more, 140 nm or more, 150 nm or more, 160 nm or more, 170 nm or more, 180 nm or more, 190 nm or more, or 200 nm or more. In certain aspects, the average HGN diameter is 200 nm or less, 190 nm or less, 180 nm or less, 170 nm or less, 160 nm or less, 150 nm or less, 140 nm or less, 130 nm or less, 120 nm or less, 110 nm or less, 100 nm or less, 90 nm or less, 80 nm or less, 70 nm or less, 60 nm or less, 50 nm or less, 40 nm or less, 30 nm or less, 20 nm or less, or 10 nm or less.

As will be appreciated, the diameters of individual HGNs produced according to subject methods will vary around the average diameter. In some embodiments, the diameters of the HGNs produced will vary around the average diameter (e.g., any of the average diameters provided in the preceding paragraph) by 20% or less, 17.5% or less, 15% or less, 12.5% or less, 10% or less, 7.5% or less, 5% or less, or 2.5% or less.

The average diameter of HGNs produced according to the methods of the present disclosure may be readily confirmed using any suitable approach. For example, the average diameter may be confirmed using approaches such as transmission-mode scanning electron microscopy (tSEM, e.g., using an FEI Quanta 3D Dual beam SEM), high-resolution transmission electron microscopy (HRTEM, e.g., using an FEI UT Tecnai HRTEM microscope operated at 200 kV accelerating voltage), non-limiting examples of which are described in the Experimental section below.

HGNs produced according to the methods of the present disclosure may have a desired aspect ratio (that is, the ratio of HGN outer diameter to shell thickness), which aspect ratio may be determined based on, e.g. the concentration of the cobalt salt, capping agent, and/or reducing agent during Co NP synthesis. See, e.g., Schwartzberg et al. (2006) *J. Phys. Chem. B* 110:19935. The present inventors have found that HGN aspect ratio—like Co NP diameter—is inversely related to the reaction temperature provided during Co NP synthesis. That is, a higher aspect ratio may be achieved by selecting a lower synthesis temperature, and a lower aspect ratio may be achieved by selecting a higher synthesis temperature. In some embodiments the average aspect ratio of HGNs produced according to the subject methods is from about 3 to about 10, e.g., from about 3 to about 8, such as from about 4 to about 7.

HGNs produced according to the methods of the present disclosure may exhibit optical properties, photothermal properties, and/or the like determined by their average diameter and/or aspect ratio, which in turn is determined by the pre-selected diameter of the Co NPs produced under the Co NP synthesis conditions at the selected temperature. In certain aspects, the produced HGNs exhibit a surface plasmon resonance (SPR) absorption with a maximum peak position in the visible range, e.g., from about 400 to about 700 nm. In some embodiments, the produced HGNs exhibit an SPR absorption with a maximum peak position in the infrared range, e.g., from about 700 nm to about 1 m. In certain aspects, the produced HGNs exhibit an SPR absorption with a maximum peak position in the near-infrared (near-IR) range, e.g., from about 700 nm to about 2500 nm. In some embodiments, the produced HGNs exhibit an SPR absorption with a maximum peak position of from about 400 to about 1200 nm (e.g., from about 565 to about 850 nm), such as from 420 to 1180 nm, from 440 to 1160 nm, from 460 to 1140 nm, from 480 to 1120 nm, from 500 to 1100 nm, from 520 to 1080 nm, from 540 to 1060 nm, from 560 to 1040 nm, from 580 to 1020 nm, from 600 to 1000 nm, from 620 to 980 nm, from 640 to 960 nm, from 660 to 940 nm, from 680 to 920 nm, from 700 to 900 nm, from 720 to 880 nm, from 740 to 860 nm, from 760 to 840 nm, or from 780 to 820 nm (e.g., about 800 nm).

In some embodiments, methods that include producing HGNs using the Co NPs as scaffolds may further include attaching a moiety (e.g., a targeting moiety) to the surface of the HGNs. In certain aspects, a targeting moiety selected from an antibody, a ligand, an aptamer, a nucleic acid, and a small molecule, is attached to the surface of the HGNs. By "targeting moiety" is meant a moiety that directly or indirectly binds to a target. Targets of interest include analytes (e.g., proteins, nucleic acids, small molecules, or the like), cells (e.g., cells in an in vitro or in vivo environment), and the like.

In certain aspects, the HGNs include a targeting moiety (e.g., an antibody, cell surface receptor ligand, or the like) that binds to a molecule on the surface of a target cell in vitro or in vivo. Such HGNs find use in research, diagnostic, and/or therapeutic applications. In some embodiments, the target cell is a cancer cell. By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a primary tumor, a metastatic tumor, and the like. In some embodiments, the HGNs include a targeting moiety (e.g., an antibody, cell surface receptor ligand, or the like) that binds to a tumor-associated or tumor-specific cell surface molecule, e.g., cell surface receptor, membrane protease, and the like. By "tumor-associated cell surface molecule" is meant a cell surface molecule expressed on malignant cells with limited expression on cells of normal tissues, a cell surface molecule expressed at much higher density on malignant versus normal cells, or a cell surface molecule that is developmentally expressed.

Any tumor-associated cell surface molecule or tumor-specific cell surface molecule may be targeted by the HGNs of the present disclosure. In certain aspects, the target on the cancer cell surface to which the targeting moiety of the HGNs binds is HER2, CD19, CD22, CD30, CD33, CD56, CD66/CEACAMS, CD70, CD74, CD79b, CD138, Nectin-4, Mesothelin, Transmembrane glycoprotein NMB (GPNMB), Prostate-Specific Membrane Antigen (PSMA), SLC44A4, CA6, CA-IX, $\alpha v\beta 1$ integrin, $\alpha v\beta 3$ integrin, $\alpha v\beta 5$ integrin, $\alpha v\beta 6$ integrin, $\alpha 5\beta 1$ integrin, C—X—C chemokine receptor type 4 (CXCR4), cytotoxic T-lymphocyte-associated protein 4 (CTLA-4), neuropilin-1 (NRP1), matriptase, or any other tumor-associated or tumor-specific cell surface molecule of interest.

A variety of suitable approaches exist for attaching a targeting moiety to HGNs. In one non-limiting example, thiol-based surface functionalization of the HGNs may be employed. For example, bifunctional SH-PEG-COOH linkers have been employed to conjugate antibodies to HGNs, the details of which may be found, e.g., in Liu et al. (2015) *Nanoscale Res. Lett.* 10:218. Briefly, the SH-PEG-COOH linker may be reacted with the HGNs, followed by addition of N-(3-dimethylaminopropyl)-N-ethylcarbodiimidehydrochloride (EDC) and N-hydroxy succinimide (NHS) to activate the carboxyl terminal of PEG, followed by combining the PEGylated HGNs with the antibody of interest.

Also provided are HGNs produced according to any of the methods of the present disclosure. The HGNs may be present in a container, such as a vial, tube, plate (e.g., 96-well or other plate), flask, or the like. In some embodiments, the HGNs are present in a liquid medium, e.g., water or other suitable liquid storage medium. In certain aspects, the HGNs are present in a lyophilized form.

The present disclosure also provides methods of using the produced HGNs in a variety of applications. Non-limiting examples of such applications include surface-enhanced Raman scattering (SERS),[5-6] photothermal therapy (PTT),[7-8] plasmonic enhanced photoelectric conversion, chemical catalysis[9] and biosensors.[10-15]

In one example, HGNs produced according to the methods of the present disclosure are used for photothermal therapy (PTT). PTT involves embedding nanoparticles within tumors, which nanoparticles generate heat in response to exogenously applied laser light, thereby killing tumor cells in the vicinity of the nanoparticles. The preferred mediators of PTT are gold-based nanoparticles because they offer: (1) simple gold-thiol bioconjugation chemistry for the attachment of desired targeting molecules; (2) biocompatibility, (3) efficient light-to-heat conversion; (4) small diameters that enable tumor penetration upon systemic delivery, and (5) the ability to be tuned to absorb near-infrared light, which penetrates tissue more deeply than other wavelengths of light. PTT may be used in combination with other therapies, such as chemotherapy, gene regulation, and immunotherapy, for enhanced anti-tumor effects. Details regarding PTT approaches that may be practiced employing HGNs produced according to methods of the present disclosure may be found, e.g., in Riley R. S. & Day, E. S. (2017) *Wiley Interdiscip. Rev. Nanomed. Nanobiotechnol.* 2017 9(4); Melancon et al. (2008) *Mol. Cancer Ther.* 7:1730; and Lu et al. (2009) *Clin. Cancer Res.* 15:876.

Accordingly, provided are methods that include administering HGNs produced according to the methods of the present disclosure to an individual in need thereof. In some embodiments, the individual in need thereof is in need of photothermal therapy (PTT), e.g., an individual having cancer. In certain aspects, the HGNs include a targeting moiety that binds to a molecule on the surface of a target cell (e.g., a cancer cell) of the individual.

Compositions

Also provided are compositions that include the Co NPs or HGNs of the present disclosure. The compositions may include any of the Co NPs or HGNs described herein. In certain aspects, the compositions include the Co NPs or HGNs present in a liquid medium. The liquid medium may be an aqueous liquid medium, such as water, a buffered solution, and the like. One or more additives such as a salt (e.g., NaCl, MgCl2, KCl, MgSO4), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a solubilizing agent, a detergent (e.g., a non-ionic detergent such as Tween-20, etc.), glycerol, a chelating agent, and the like may be present in such compositions.

Pharmaceutical compositions are also provided. The pharmaceutical compositions include any of the HGNs of the present disclosure, and a pharmaceutically acceptable carrier. The pharmaceutical compositions generally include a therapeutically effective amount of the HGNs, e.g., for use in photothermal therapy. By "therapeutically effective amount" is meant a dosage sufficient to produce a desired result, e.g., an amount sufficient to effect beneficial or desired therapeutic (including preventative) results, such as a reduction in a symptom of a disease or disorder (e.g., a cell proliferative disorder such as cancer), as compared to a control. An effective amount can be administered in one or more administrations.

The HGNs of the present disclosure can be incorporated into a variety of formulations for therapeutic administration, e.g., oral, parenteral, or other routes of administration. More particularly, the HGNs can be formulated into pharmaceutical compositions by combination with appropriate, pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the HGNs suitable for administration to a patient (e.g., suitable for human administration) are generally sterile and may further be free of detectable pyrogens or other contaminants contraindicated for administration to a patient according to a selected route of administration.

The HGNs can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions that include the HGNs may be prepared by mixing the HGNs having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

Kits

As summarized above, the present disclosure provides kits. In some embodiments, provided are kits that include one or more (e.g., each) of a cobalt salt, a capping reagent, and a reducing reagent suitable for producing cobalt nanoparticles. Such kits further include instructions for using the one or more of a cobalt salt, a capping reagent, and a reducing reagent to produce cobalt nanoparticles of a pre-selected diameter based on the temperature of the Co NP synthesis reaction. For example, the kits may include instructions (e.g., in the form of a list, table, chart, or the like) indicating the temperature that should be provided to the synthesis reaction to produce Co NPs of the desired pre-selected diameter. Such instructions may indicate the inverse relationship between synthesis temperature and pre-selected diameter. In certain aspects, the instructions are for producing two or more populations of Co NPs having different desired pre-selected diameters based on different temperatures being provided to the respective Co NP synthesis reactions.

In certain aspects, provided are kits that include cobalt nanoparticles (Co NPs) of a desired average diameter produced according to any of the methods of the present disclosure. The kits may further include instructions for using the Co NPs to produce hollow gold nanospheres (HGNs), e.g., via a galvanic exchange reaction or other suitable reaction for producing HGNs from Co NPs. In some embodiments, such kits include two or more populations of Co NPs (provided in the same container or separate containers) each having different average diameters and produced using different synthesis temperatures according to any of the methods of the present disclosure. The kits that include Co NPs may further include one or more reagents for producing HGNs from the Co NPs. As just one example, such kits may include one or more reagents for producing HGNs by galvanic exchange. In certain aspects, the one or more reagents for producing HGNs by galvanic exchange includes $HAuCl_4$. The kits may further include one or more reagents and accompanying instructions for functionalizing the surface of the HGNs, e.g., by attaching a linker and/or moiety (e.g., a targeting moiety such as an antibody, or the like) to the surface of the HGNs. In one example, the kits include a thiol-based surface functionalization reagent, e.g., a bifunctional thiol-based linker, such as an SH-PEG-COOH linker. In some embodiments, the targeting moiety is one that binds to a molecule on the surface of a target cell (e.g., a cancer cell) in vitro or within an individual.

In some embodiments, provided are kits that include hollow gold nanospheres (HGNs) produced according to the methods of the present disclosure, or a pharmaceutical composition including such HGNs. Such kits may include instructions for employing the HGNs in a variety of research, diagnostic and/or therapeutic applications. In certain aspects, the kits include instructions for using the HGNs to detect an analyte in vitro (e.g., biosensing, such as in vitro analyte detection, or the like) or in vivo (e.g., in vivo imaging, such as in vivo tumor imaging, or the like). Alternatively, or additionally, the kits may include instructions for administering the HGNs to an individual in need thereof, e.g., an individual in need of photothermal therapy (PTT), such as an individual having cancer. Kits that include HGNs for therapeutic applications may include the HGNs present in one or more (e.g., two or more) unit dosages.

Kits that include HGNs may further include one or more reagents and accompanying instructions for functionalizing the surface of the HGNs, e.g., by attaching a linker and/or moiety (e.g., a targeting moiety such as an antibody, or the like) to the surface of the HGNs. In one example, the kits include a thiol-based surface functionalization reagent, e.g., a bifunctional thiol-based linker, such as an SH-PEG-COOH linker. In some embodiments, the targeting moiety is one that binds to a molecule on the surface of a target cell (e.g., a cancer cell) in vitro or within an individual. Components of the kits may be present in separate containers, or multiple components may be present in a single container. For example, in a kit that includes reagents for producing Co NPs and/or reagents for producing HGNs, two or more of such reagents may be provided in the same tube, or may be provided in different tubes.

In addition to the above-mentioned components, and as described above, a subject kit may further include instructions for using the components of the kit, e.g., to practice the methods of the present disclosure. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

Experimental

Introduction

In this work, a facile synthesis is reported that allows alteration of the diameter of cobalt nanoparticles (Co NPs) and, if desired, corresponding hollow gold nanospheres (HGNs) produced therefrom, through thermodynamic control. Specifically, a range of reaction temperatures were investigated and it was surprisingly found that the diameter of the cobalt scaffolds was inversely correlated with the reaction temperature. In particular, cobalt scaffolds produced at 10° C. had adiameter of 145 nm while cobalt scaffolds produced at 80° C. had a diameter of 34 nm. As a result, HGNs produced using a subsequent galvanic exchange showed a wide SPR range from 850 nm to 565 nm. The optical properties were characterized using UV-Visible spectroscopy. A mechanism behind the temperature-dependent HGN synthesis can potentially be explained by the thermodynamics of homogeneous nuclei formation of the cobalt scaffold. To help gain a better understanding of the dependence of optical properties of the resultant HGNs on their structure, discrete dipole approximation (DDA) calculations were performed. These calculations indicate that the scattering contribution is directly proportional to the particle size of HGNs. It was concluded that reaction temperature critically affects the nucleation of the cobalt scaffolds and thereby subsequent HGN growth, final structure, and resultant optical properties.

Materials and Methods

Materials

Cobalt chloride hexahydrate ($CoCl_2 \cdot 6H_2O$, 99.99%), trisodium citrate (99%), sodium borohydride ($NaBH_4$, 99%), citric acid (99%), Milli-Q deionized (DI) water (18 MΩ·cm), and chloroauric acid trihydrate ($HAuCl_4 \cdot 3H_2O$, ACS reagent grade) were obtained from Fisher Scientific.

Characterization of HGNs

The structure and morphology of the HGNs were characterized with transmission-mode scanning electron microscopy (tSEM, FEI Quanta 3D Dual beam SEM), high-resolution transmission electron microscopy (HRTEM, FEI UT Tecnai HRTEM microscope operated at 200 kV accelerating voltage), and dynamic light scattering (DLS, DynaPro NanoStar, Wyatt Technology) to analyze the particle size and shell thickness of the HGN samples. The optical properties of the temperature-dependent HGN samples were characterized using UV-visible spectroscopy (Agilent Tech. Cary 60 UV-Vis spectrometer).

Simulation of Optical Properties of HGNs

The discrete dipole approximation (DDA) method is widely used to calculate the SPR of gold nanostructures.[44-45], [46] The target nanostructure, e.g. HGN, is discretized as a finite cubic array of N polarizable cells. Each dipole is located at $\vec{r}_i$ with the electric polarizability $\alpha_i$, which can be obtained from the dielectric function.[44] The induced electric dipole $\vec{P}_i$ at position $\vec{r}_i$ is determined by $$\vec{P}_i = \alpha_i \vec{E}_i \quad (1)$$

where $\vec{E}_i$ is the total electric field at $\vec{r}_i$ and it can be written as $$\vec{E}_i = \vec{E}_{inc,i} - \sum_{j \neq i} \vec{A}_{ij} \vec{P}_j \quad (2)$$

Here, $\vec{E}_{inc,i}$ is the incident field, and can be expressed as $$\vec{E}_{inc,i} = E_0 \exp(i\vec{k} \cdot \vec{r}_i - i\omega t) \quad (3)$$

$\vec{k}$ denotes the wave vector, $k \equiv 2\pi/\lambda$, where $\lambda$, t, ω are the wavelength, the time, the angular frequency of the incident light, respectively. $\vec{A}_{ij}$ is the transfer function tensor describing the electric field at position i created by an oscillating dipole at position j.[47] It can be expressed as $$\vec{A}_{ij} = \frac{\exp(ikr_{ij})}{r_{ij}} \left[ k^2(\hat{r}_{ij}\hat{r}_{ij} - I) + \frac{ikr_{ij} - 1}{r_{ij}^2}(3\hat{r}_{ij}\hat{r}_{ij} - I) \right] \quad (4)$$

Here, $$r_{ij} = |\vec{r}_i - \vec{r}_j|, \hat{r}_{ij} = \frac{\vec{r}_i - \vec{r}_j}{r_{ij}},$$

and I is a 3×3 identity matrix. When substituting Eq 2 and Eq 4 into Eq 1 and also defining $A_{ii} = \alpha_i^{-1}$, the system of equations as below can be generated $$\sum_{j=1}^{N} A_{ij} \vec{P}_j = \vec{E}_{inc,i} \quad (5)$$

Then, the extinction ($Q_{ext}$), absorption ($Q_{abs}$) and scattering ($Q_{sca}$) efficiency factors can be calculated using the following formula:

$$Q_{ext} = \frac{4k}{|\vec{E}_0|^2 a_{eff}^2} \text{Im} \sum_{i=1}^{N} \left( \vec{E}_{inc,i}^* \cdot \vec{P}_i \right) \quad (6)$$

$$Q_{ext} = \frac{4k}{|\vec{E}_0|^2 a_{eff}^2} \sum_{i=1}^{N} \left\{ \text{Im}[\vec{P}_i \cdot (\alpha_i^{-1})^* \vec{P}_i^*] - \frac{2}{3} k^3 \cdot |\vec{P}_i|^2 \right\} \quad (7)$$

$$Q_{sca} = Q_{ext} - Q_{abs} \quad (8)$$

where $a_{eff}$ is defined as effective radius of a sphere of equal volume. All extinction coefficient calculations were carried out using the latest version of DDSCAT 7.3 software.

For the DDA accuracy to be validated in the course of calculation, the criterion $|m|kd < 0.5$ was adequately satisfied, where m is the complex refractive index of the target material and d is the inter-dipole separation. The dielectric function of gold was chosen from Johnson and Christy's study and the refractive index of the surrounding medium was chosen as that of water.[48] The location of each dipole in the target geometry was created using Matlab software, and then, the shape.dat files for hollow spheres with different diameters could be generated.

Synthesis of HGNs Through Reaction Temperature Control

All glassware was cleaned with aqua regia, and then further rinsed with high purity water and ethanol to exclude any contaminants. The reaction temperatures of the HGN syntheses ranged from 10 to 80° C. and were controlled by a water or ice bath. Air-free cobalt scaffold syntheses were performed on a Shlenck line in order to prevent oxidation and aggregation.

A double-neck round bottom flask was filled with 100 mL of DI water, 100 μL of 0.4 M $CoCl_2$ aqueous solution, and 100 μL of 0.1 M trisodium citrate aqueous solution. The flask was sealed and the solution was vacuumed for 5 minutes. $N_2$ gas was then pumped into the solution. A 400 μL of 0.1 M $NaBH_4$ aqueous solution was then quickly injected into the flask at once while swirling by hand or stirring by stir bar. The flask was continuously swirled until the clear solution changed color to either brown or grey indicating the successful synthesis of Co NPs. Immediately following the color change, a 175 μL of 0.1 M citric acid solution was injected into the reaction solution to scavenge the excess sodium borohydride and prevent aggregation of the Co NPs. The solution was then allowed to react for 10 minutes under $N_2$ to allow the Co NPs to grow for the further utilization as the cobalt scaffold solution.

90 mL of the cobalt scaffold solution was then poured immediately into a beaker containing 30 mL of DI-water that contained 60 μL of 0.1 M $HAuCl_4$ aqueous solution under air atmosphere, and then rapidly swirled by hand. Rapid hand swirling was performed in order to prevent the magnetic Co NPs from aligning with the induced magnetic field of the stir bar. The formation of chains and backbone-like structures was observed after magnetic stirring. These undesirable structures were not observed with hand mixing. The color of the solution then changed to purple, blue, or green indicating the formation of HGNs through galvanic replacement between the cobalt and the gold. The final color of the HGN solution and the SPR depends on the particle size and shell thickness. HGNs absorbing at bluer wavelengths appear red or purple and those absorbing at longer wavelengths appear blue or green.

Results

Figure 2:
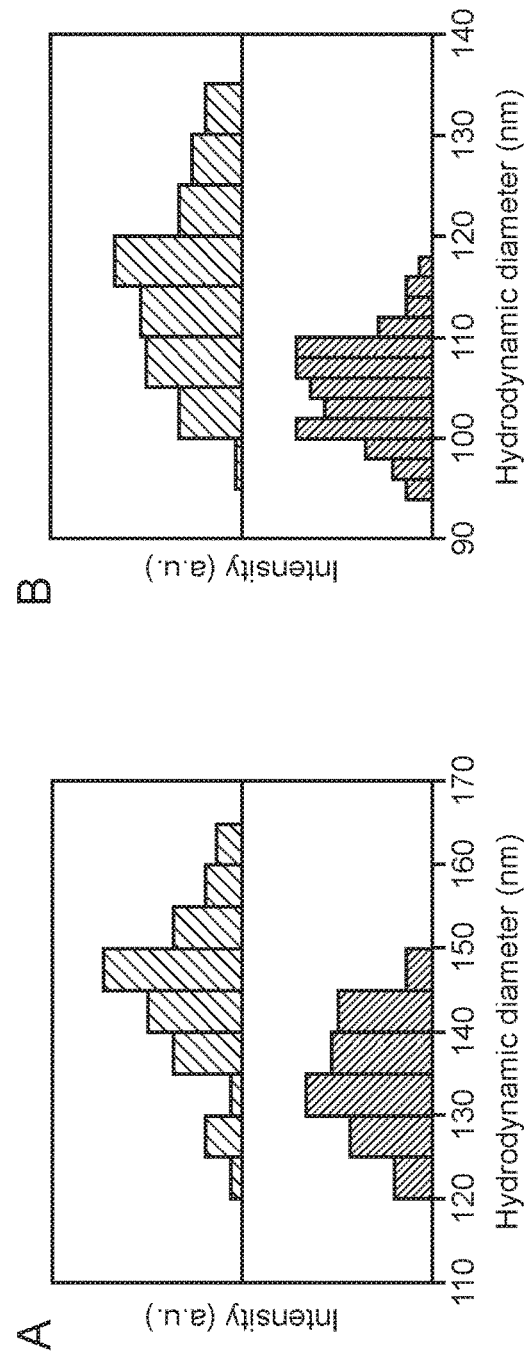
FIG. 2, panels A-H, shows a series of bar graphs indicating dynamic light scattering (DLS) size distribution of cobalt scaffolds (gray bars) and HGNs (red bars) at different reaction temperatures. (A) 10° C., (B) 20° C., (C) 30° C., (D) 40° C., (E) 50° C., (F) 60° C., (G) 70° C. and (H) 80° C.
Figure 2:
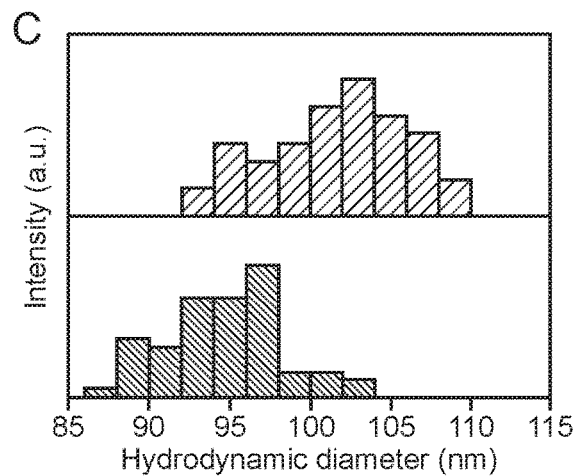
Figure 2:
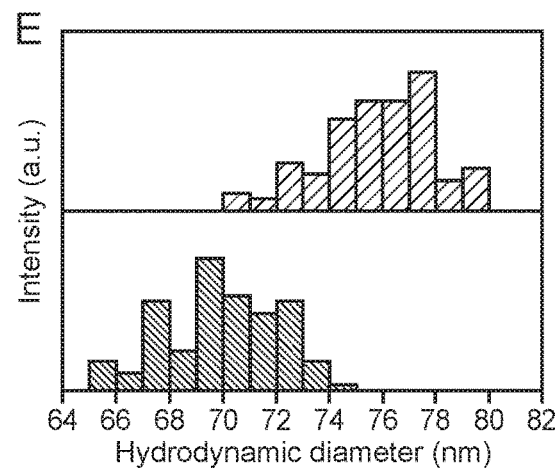
Figure 2:
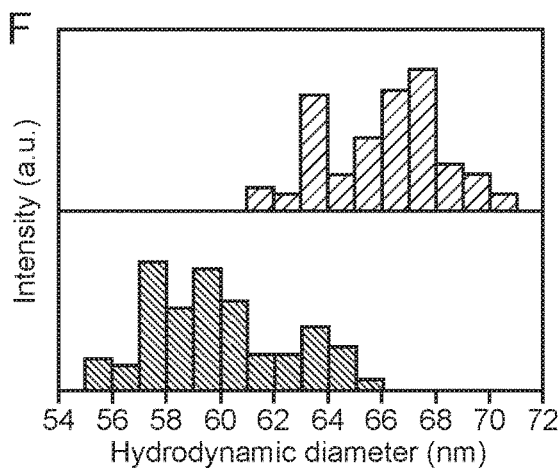
Figure 2:
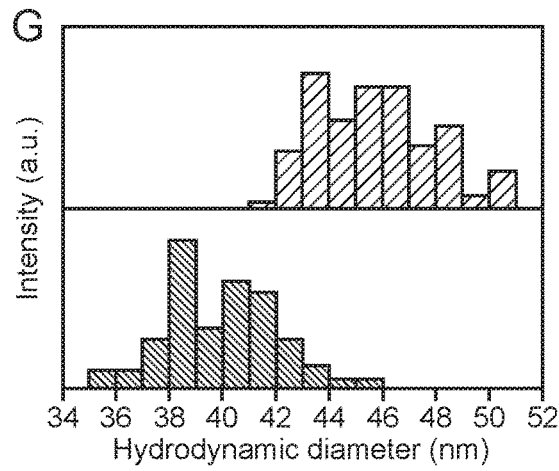
Figure 2:
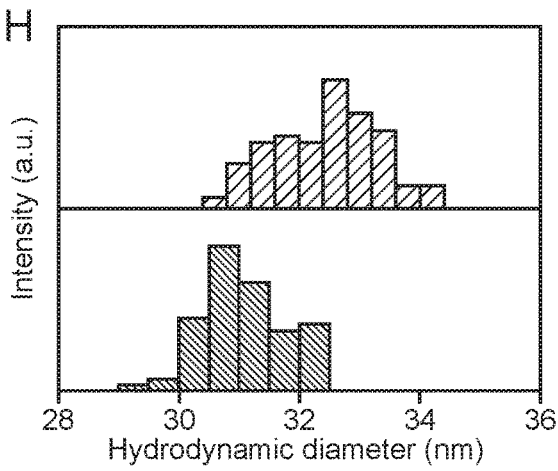

The size variations of cobalt scaffolds and HGNs were investigated by DLS measurements. FIG. 2 displays the DLS data of cobalt scaffolds that were prepared under different reaction temperatures. The measured average hydrodynamic diameters of Co NPs were 145.0±18.5, 115.4±16.7, 101.7±10.6, 87.3±10.1, 75.8±6.8, 66.2±6.3, 45.8±5.7 and 33.6±4.5 nm for reaction temperature of 10, 20, 30, 40, 50, 60, 70, and 80° C., respectively.

After the HGNs were synthesized using the cobalt scaffolds through galvanic exchange, the measured average hydrodynamic diameters of HGNs were 134.5±17.6, 104.9±15.5, 94.7±12.7, 80.9±10.4, 70.0±6.3, 60.3±7.5, 39.9±8.1, and 31.1±4.3 nm for reaction temperature of 10, 20, 30, 40, 50, 60, 70, and 80° C., respectively. It is observed that the averaged hydrodynamic diameters of HGNs are smaller than their corresponding cobalt scaffolds.

Figure 3:
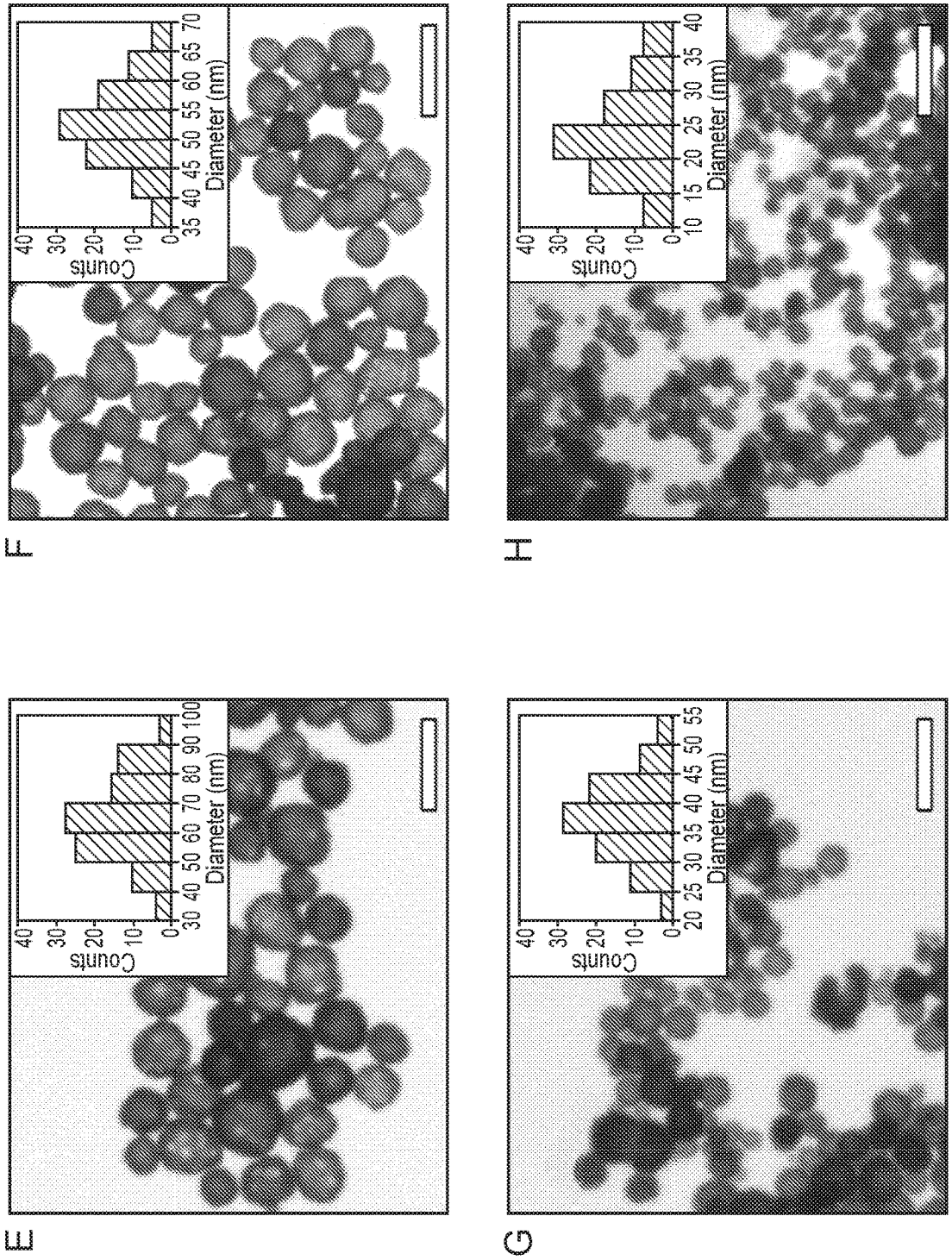
FIG. 3, panels A-H, shows transmission-mode scanning electron microscopy (tSEM) images of the HGNs: (A) HGN-10, (B) HGN-20, (C) HGN-30, (D) HGN-40, (E) HGN-50, (F) HGN-60, (G) HGN-70 and (H) HGN-80. Scale bars=100 nm. The insets of histograms show the HGN diameter distribution.

Electron microscopy was used to better determine the particle size and shell thickness of HGNs, . FIG. 3 shows the tSEM images of the HGNs that were synthesized with reaction temperatures ranging from 10 to 80° C., denoted as HGN-X, where X represents the reaction temperature for cobalt scaffold formation (in ° C.). Uniform spherical HGNs were observed in all the samples. As measured from tSEM, the average diameters of the corresponding HGN samples were 122.5±13.0, 101.0±13.7, 87.8±13.1, 70.6±15.5, 65.5±11.0, 50.8±9.7, 35.0±7.3, and 24.3±6.8 nm, which were also shown in the corresponded histograms as the insets. These measurements are consistent with the trends observed in DLS measurements. The HGN diameters according to DLS were larger by about ~5-20% since DLS measures hydrodynamic diameter.

Figure 4:
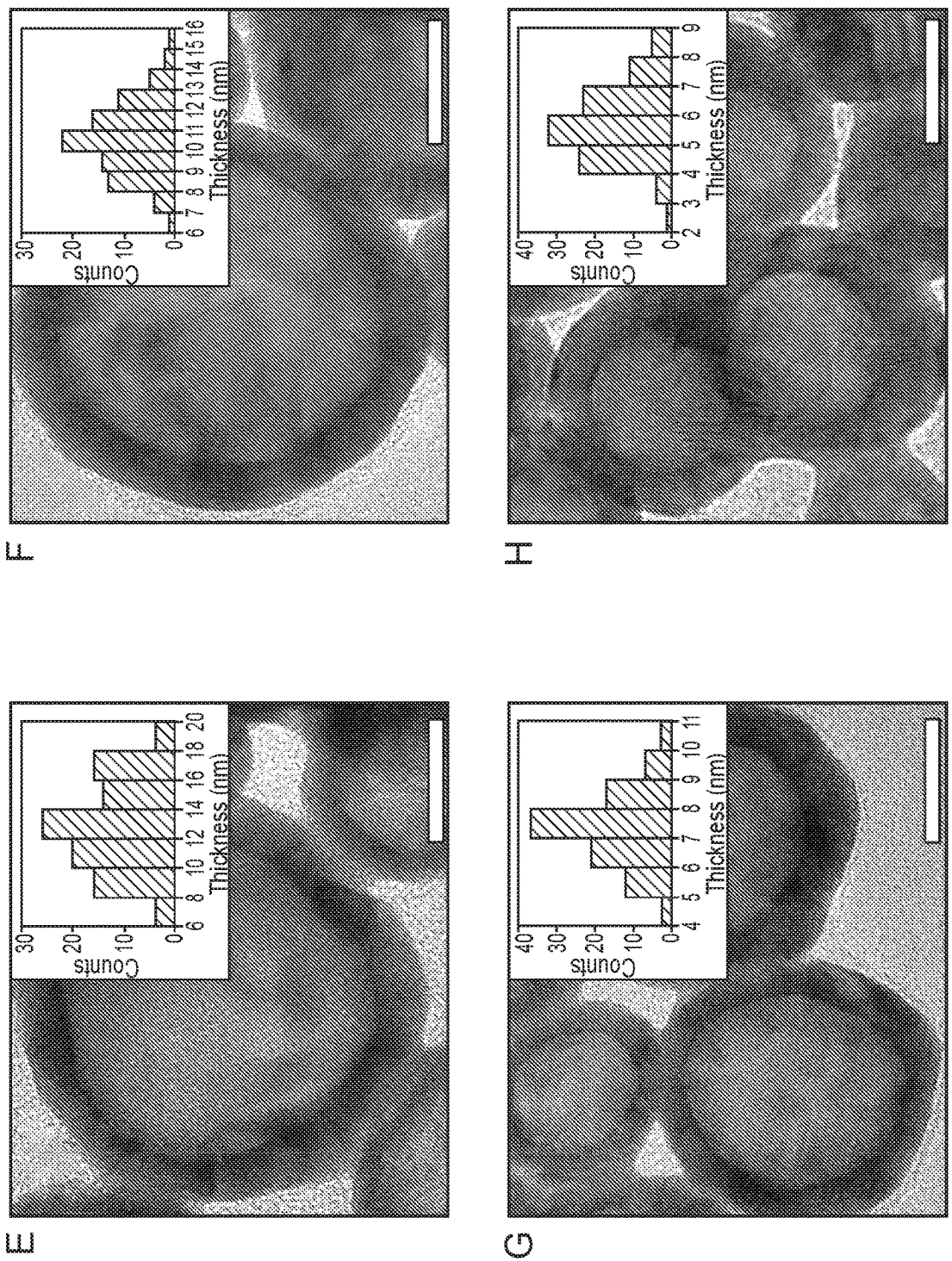
FIG. 4, panels A-H, shows high resolution transmission electron microscopy (HRTEM) images of the HGNs: (A) HGN-10, (B) HGN-20, (C) HGN-30, (D) HGN-40, (E) HGN-50, (F) HGN-60, (G) HGN-70 and (H) HGN-80. Scale bars=(A-D) 20 nm and (E-H) 15 nm. The insets of histograms show the HGN shell thickness distribution.
Figure 5:
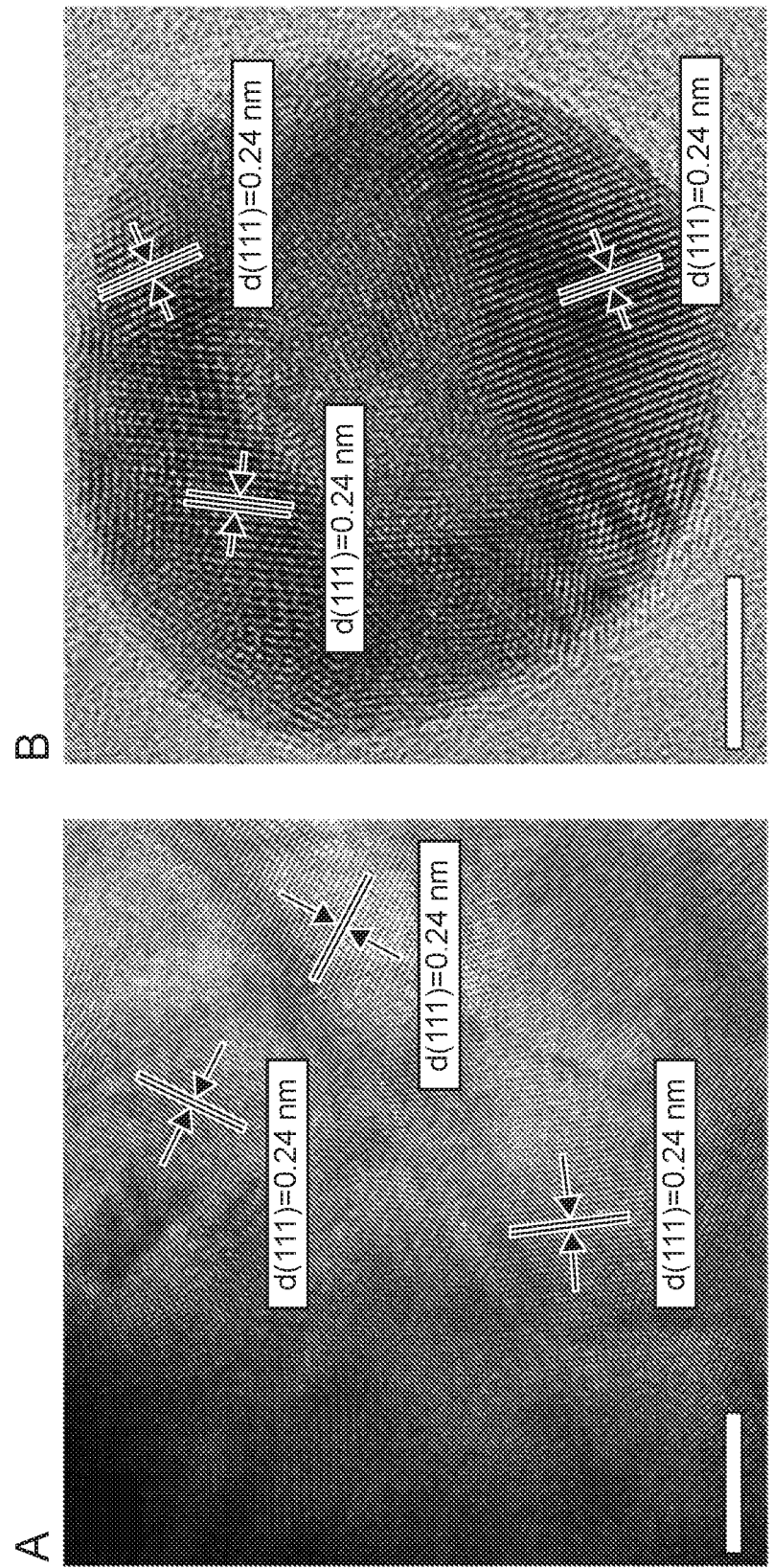
FIG. 5, panels A and B, shows HRTEM images of HGN-10 (panel a) and HGN-80 (panel b) showing the lattice fringes in the shell structures. Scale bars are 5 nm.

The shell thickness of each HGN sample was further characterized by HRTEM. As shown in FIG. 4, the shell thickness of HGN-10, HGN-20, HGN-30, HGN-40, HGN-50, HGN-60, HGN-70 and HGN-80 were 18.4±4.0, 15.0±2.7, 14.8±3.4, 13.9±2.1, 13.3±1.5, 10.7±1.3, 7.5±1.1, and 5.4±1.1 nm, respectively. The distribution of shell thickness of the corresponding HGN samples were also shown as the histograms of the insets. In addition, the well-resolved lattice fringes and similar interlayer spacing of these polycrystalline HGN samples could be clearly seen in the HRTEM images. As seen in FIG. 5, the lattice fringe images of the largest and smallest HGN samples, which showed that the interlayer spacings of the polycrystalline shells were all measured as 0.24 nm. The aspect ratios of diameter/shell thickness of the as-synthesized HGN samples were 6.7, 6.7, 5.9, 5.1, 4.9, 4.7, 4.7 and 4.5 nm for HGN-10, HGN-20, HGN-30, HGN-40, HGN-50, HGN-60, HGN-70 and HGN-80, respectively.

Figure 6:
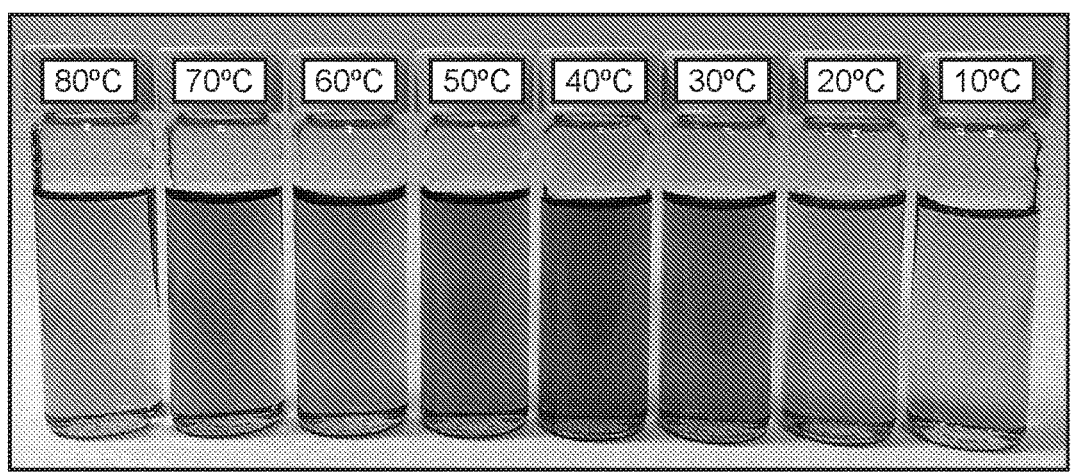
FIG. 6, panels A and B, shows a photograph of the as-prepared HGN sample solutions under room light (panel A) and UV-vis spectra (panel B), of the resultant HGNs from cobalt scaffolds with different sizes.
Figure 6:
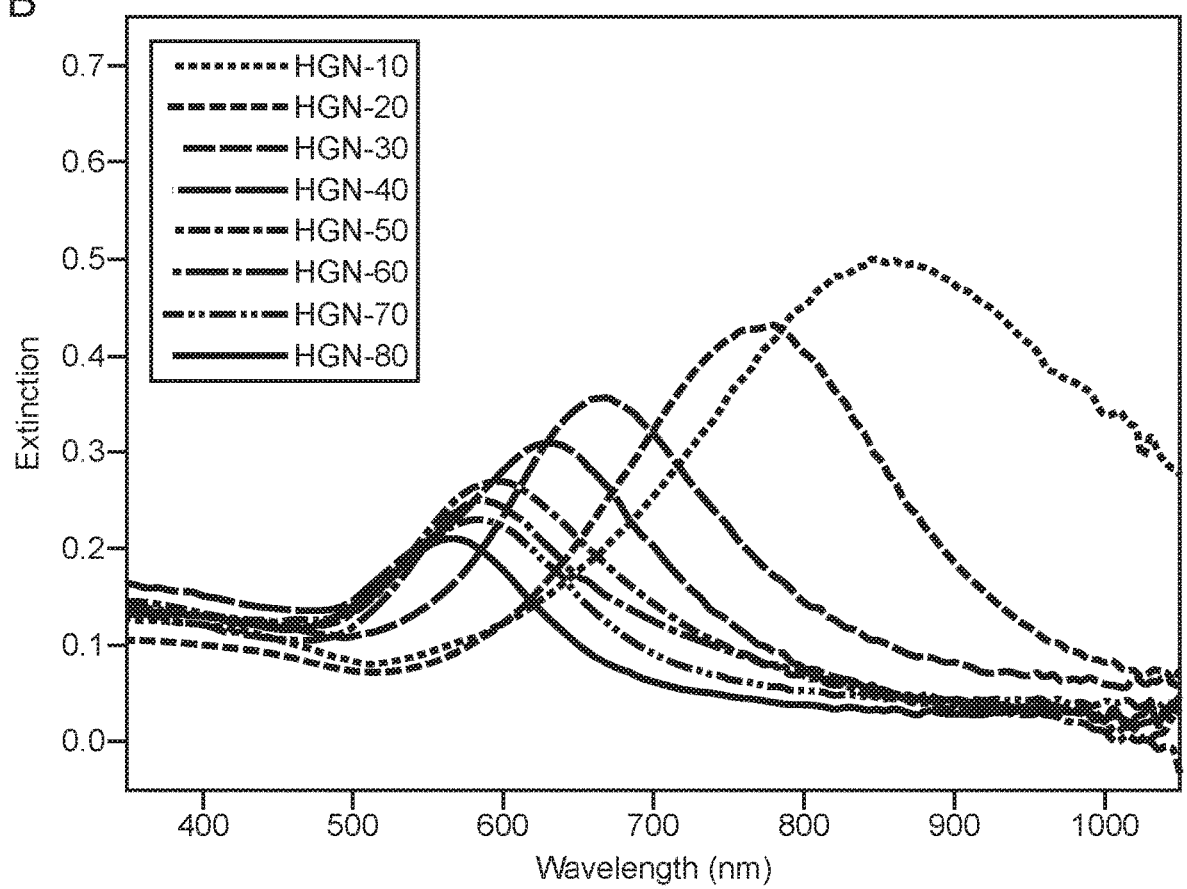

As expected, the different aspect ratios of the HGNs result in different optical properties. FIG. 6, panel a, shows a photograph of the eight HGN samples, which clearly exhibits different colors, ranging from red-purple for the highest reaction temperature (80° C.) to green for the lowest temperature (10° C.). Overall, these samples cover the entire visible to NIR regions of the spectrum. The SPR absorption spectra of the temperature-dependent HGNs were measured using UV-vis spectroscopy and are shown in FIG. 6, panel b. At a reaction temperature of 10° C., the maximum SPR absorption peak was 850 nm. At a reaction temperature of 80° C., the maximum SPR absorption peak was 565 nm. Interestingly, the optical intensity of the SPR absorption spectra of as-prepared HGN samples was lower at higher reaction temperatures. The ratio of concentrations between Co and Au were kept as a constant of 8:1 for all the HGN samples during the syntheses.

In order to further understand the optical properties of the HGNs, particularly the effect of temperature upon the synthesis of the cobalt scaffold, DDA calculations were performed to determine extinction spectra and the calculations compared to experimental results. Hao and co-workers have demonstrated that DDA calculation is a powerful method to study the extinction spectra and near field electromagnetic field population of HGNs.[33] In previous work, DDA calculation was utilized to investigate the optical properties of hollow gold-silver double-shell nanostructures, which showed good agreement between calculated and experimental results.[39, 49] Therefore, DDA calculations can provide critical information related to the optical properties of HGNs.

Figure 7:
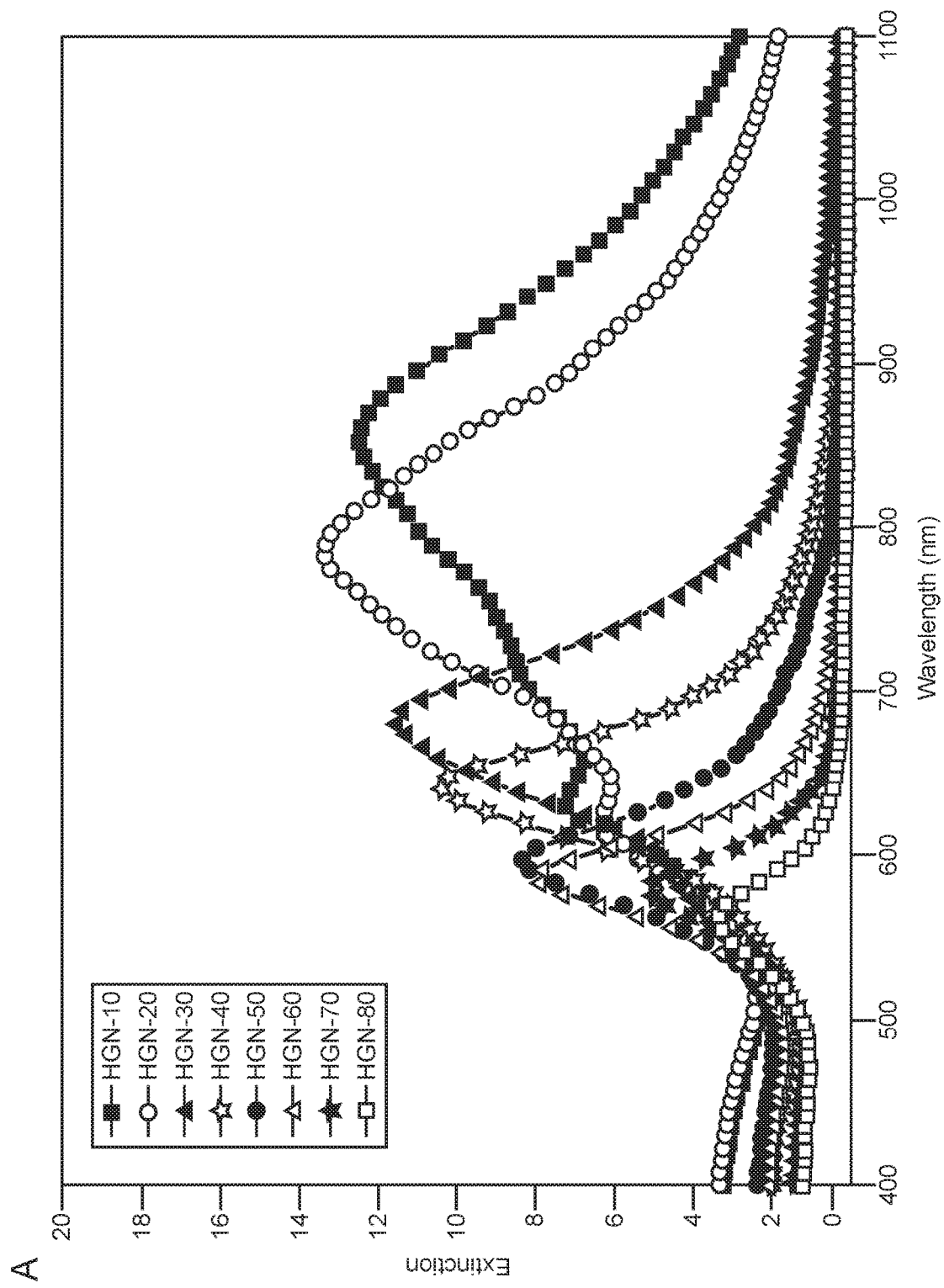
FIG. 7, panels A and B, shows DDA calculated extinction spectra of HGNs (panel A) and the efficiencies of extinction (gray bar), absorption (blue bar) and scattering (orange bar) at the SPR maximum and the particle diameter (red dot-line) of the HGNs versus the reaction temperatures of cobalt scaffold syntheses (panel B).
Figure 7:
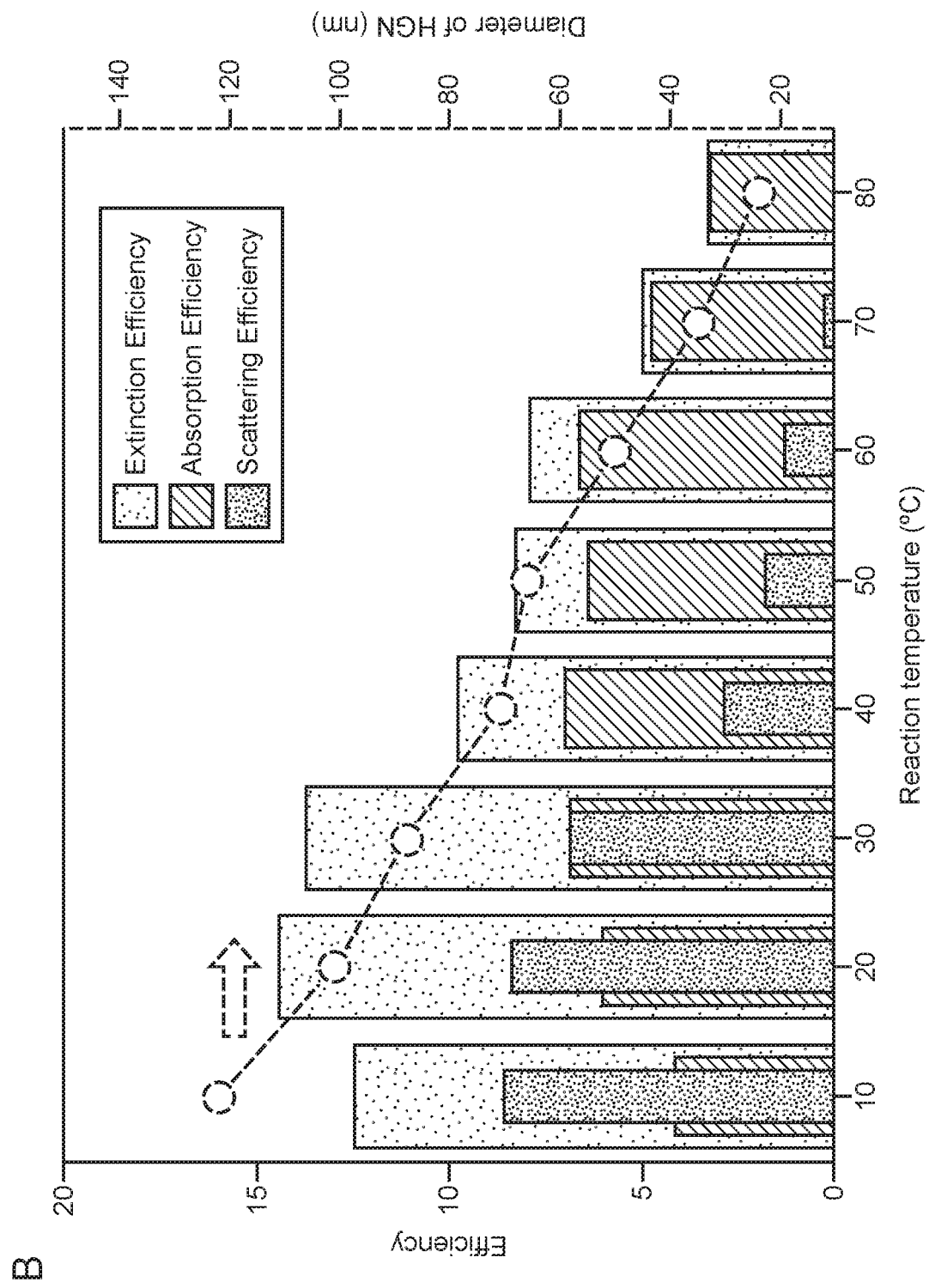

In the present study, simulated SPR spectra for the series of HGN syntheses were obtained from DDA calculations by using the particle diameter and shell thickness of the HGNs determined from tSEM images. As shown in FIG. 7, panel a, a blue shift of the SPR absorption profiles and a decrease in intensity with decreasing aspect ratio were observed. This is consistent with the disclosed experimental data. The relative contributions from scattering and absorption to the overall extinction spectra for different HGNs have also been calculated, as shown in FIG. 7, panel b. The contributions of scattering efficiencies were 67.4%, 58.3%, 50.0%, 29.2%, 22.2%, 16.5%, 5.0% and 2.8% for HGN-10, HGN-20, HGN-30, HGN-40, HGN-50, HGN-60, HGN-70 and HGN-80. The variations of the particle diameters of the HGNs are also incorporated as a red dot-line profile in FIG. 7, panel b, for comparison. It is apparent that the scattering efficiencies negatively correlate with the reaction temperature of cobalt scaffold synthesis increases, resulting in the lower diameter of the cobalt scaffold and the resultant HGN. Table 1 summarizes the SPR peak position, diameter, and shell thickness of each HGN sample based on experimental results and DDA calculations.

TABLE 1

Summary of experimental and DDA calculation results of HGNs.

| Reaction temperature (° C.) | Experimental results from tSEM and HRTEM images | | | Simulation results from DDA calculations | | |
|---|---|---|---|---|---|---|
| | Maximum of SPR (nm) | Diameter (nm) | Shell thickness (nm) | Maximum of SPR (nm) | Diameter (nm) | Shell thickness (nm) |
| 10 | 850 | 122.5 ± 13.0 | 18.4 ± 4.0 | 852 | 120 | 14 |
| 20 | 780 | 101.0 ± 13.7 | 15.0 ± 2.7 | 781 | 100 | 12 |
| 30 | 680 | 87.8 ± 13.1 | 14.8 ± 3.4 | 681 | 85 | 11 |
| 40 | 635 | 70.6 ± 15.5 | 13.9 ± 2.1 | 640 | 70 | 10 |
| 50 | 594 | 65.5 ± 11.0 | 13.3 ± 1.5 | 598 | 64 | 10 |
| 60 | 585 | 50.8 ± 9.7 | 10.7 ± 1.3 | 584 | 54 | 9 |
| 70 | 580 | 35.0 ± 7.3 | 7.5 ± 1.1 | 577 | 36 | 6 |
| 80 | 565 | 24.3 ± 6.8 | 5.4 ± 1.1 | 563 | 25 | 5 |

As demonstrated herein, control of the nucleation and growth processes of cobalt scaffolds can be used to control the particle size of HGNs. During the synthesis of cobalt scaffold at reaction temperatures in the range of about 10-30° C., the color of the reaction solution turned from colorless to gray following a fast injection of NaBH$_4$. However, at reaction temperatures above 40° C., the reaction solution showed a brown color after NaBH$_4$ injection. After the as-prepared cobalt scaffold solutions were exposed to an air atmosphere, they turned colorless in a few minutes. This phenomenon has been suggested to be indicative of the oxidation of the cobalt scaffold.[41-42, 50-51] The fast measurement of DLS revealed the size of the cobalt scaffolds, and that different particle sizes of the cobalt scaffolds resulted from synthesis under different reaction temperatures. In addition, the gray color at reaction temperatures from 10-30° C. is indicative of the larger particle sizes of the cobalt scaffolds, while the brown color is indicative of smaller particle sizes.

Without being bound by theory, the effect of temperature on the size of the cobalt scaffolds may be explained by the thermodynamics of particle nucleation and growth. The process of homogeneous nuclei formation may be explained by the total free energy of the particle, which is a sum of the surface free energy and the bulk free energy. Typically, the radius r, the surface free energy γ, the free energy of the bulk crystal $\Delta G_v$, and a total free energy $\Delta G$ of a spherical particle are defined as follows:[52]

$$\Delta G = 4\pi r^2 \gamma + \frac{4}{3}\pi r^3 \Delta G_v \qquad (9)$$

$$\Delta G_v = \frac{-k_B T \ln(S)}{v} \qquad (10)$$

$$\Delta G_{crit} = \frac{4}{3}\pi \gamma r_{crit}^2 = \Delta G_{crit}^{homo} \qquad (11)$$

$$r_{crit} = \frac{-2\gamma}{\Delta G_v} = \frac{2\gamma v}{k_B T \ln(S)} \qquad (12)$$

The bulk crystal $\Delta G_v$ is dependent on temperature T, the Boltzmann's constant $k_B$, the supersaturation of solution S, and its molar volume (v), as defined in Eq 10. Since surface free energy is always positive and the crystal free energy is always negative, the maximum free energy required to form a stable nucleus by differentiating ΔG with respect to r and setting it to zero, dΔG/dr=0, gives a critical free energy as shown in Eq 11. The critical radius ($r_{crit}$) is defined in Eq 12 and corresponds to the minimum radius required for a particle to remain in solution without being re-dissolved. This depends on the surface free energy (γ), molar volume (v) and temperature (T). In the present work, the only varied parameter in the cobalt scaffold synthesis is the reaction temperature, which is inversely proportional to $r_{crit}$ in Eq 12. Therefore, the variation of the reaction temperature could modulate the $r_{crit}$ for the cobalt scaffold nucleation, leading to the well-controlled particle size distribution. Consequently, the particle size of the further obtained cobalt scaffold can be well controlled at the same time. Furthermore, thermodynamic control of the cobalt scaffold diameter leads to control of the resulting HGNs produced via a galvanic exchange reaction.

In comparison, the average diameters of the HGNs determined by tSEM results are smaller than their hydrodynamic diameter measured using DLS. This is likely due to the fact that in DLS measurements the entire ensemble of the HGNs including surface species were measured while in tSEM or TEM the surface species were not observed.[53] Interestingly, when the DLS results between Co NPs and HGNs were compared, the average diameters of HGNs are smaller overall than the corresponding Co NPs for each reaction temperature. Proposed is a possible mechanism to illustrate the size difference between HGNs and cobalt scaffold. In the first step of cobalt scaffold synthesis, the $Co^{2+}$ ion is reduced when NaBH$_4$ is injected into the mixture solution in the absence of oxygen. Afterward, as the monomer achieves super saturation, nucleation and subsequent growth occurs to form cobalt scaffolds. Subsequently, as the cobalt scaffolds are exposed under air atmosphere before mixing with HAuCl$_4$ aqueous solution, the oxidation of cobalt scaffolds may take place and start from the surface to reduce the particle size. Furthermore, when the oxidizing cobalt scaffold solution is mixed with the HAuCl$_4$ aqueous solution, the smaller cobalt scaffold can be replaced by $Au^{3+}$ through galvanic exchange to form a cobalt scaffold core Au shell structure. After complete oxidation of the cobalt scaffolds, the smaller sized HGNs as compared to the pristine cobalt scaffolds are produced. According to the obtained HR-TEM images of the lattice fringes, the interlayer spacing of 0.24 nm can be identified as the (111) planes of the fcc Au.[54-56] Therefore, there is no indication of Co metal remaining in the HGN structure.

The SPR absorption of the as-prepared HGNs exhibits a systematic blue shift from NIR to visible with increasing reaction temperature that results in decreased diameter and aspect ratio. In addition, the DDA calculation results of the HGN samples show good agreement with the SPR absorption spectra, illustrating that the obtained extinction spectra can be used to explain the change in optical properties of the HGNs upon thermodynamic control of cobalt scaffold syntheses, including both absorption and scattering.[45] DDA calculations show that the variation in absorption efficiency is small with respect to the aspect ratio while the scattering efficiency decreases with decreasing aspect ratio. Based on the Rayleigh theory, the scattering intensity is proportional to $r^6$ (where r is the particle radius), while absorption is proportional to $r^3$ for a sphere when the particle size is smaller than the wavelength.[57] The higher-order dependence on particle size makes scattering more sensitive to size variations than absorption.[57-58] The DDA calculations for the largest HGN show a weak shoulder at shorter wavelengths (FIG. 7a) This is likely due to high-order absorption of the HGNs such as the quadrupole effect included in the calculation,[38] which has also been reported in the DDA calculated extinction spectra of silver nanoshell.[59] Similar observations have been made experimentally for spherical Ag nanoparticles in colloidal solution and Au nanodisks.[60]-[61] Taken together, the results indicate that the particle size of cobalt scaffold can be well controlled by simply varying the reaction temperature, resulting in the tunable structure and optical properties of the HGN. This is important since there is strong interest in using HGNs with different particle sizes and well-defined SPR for various applications and controlled synthesis has been very challenging prior to the present disclosure. Therefore, the synthesis method described herein for cobalt scaffold with different sizes by modulating the reaction temperature provides a useful strategy to tune the particle size and properties of HGNs, which may be applicable to other hollow metal nanostructures.

REFERENCES

[1] C. Noguez, *J. Phys. Chem. C* 2007, 111, 3806.
[2] B. J. Wiley, S. H. Im, Z.-Y. Li, J. McLellan, Y. Xia, *J. Phys. Chem. B* 2006, 110, 15666.
[3] T. K. Sau, A. L. Rogach, F. Jackel, T. A. Klar, J. Feldmann, *Adv. Mater.* 2010, 22, 1805.
[4] T. K. Sau, A. L. Rogach, *Adv. Mater.* 2010, 22, 1781.
[5] A. M. Schwartzberg, T. Y. Oshiro, J. Z. Zhang, T. Huser, C. E. Talley, *Anal. Chem.* 2006, 78, 4732.
[6] A. Ceja-Fdez, T. L'opez-Luke, A. Torres-Castro, D. A. Wheeler, J. Z. Zhang, E. De la Rosa, *RSC Adv.* 2014, 4, 59233.
[7] M. P. Melancon, W. Lu, Z. Yang, R. Zhang, Z. Cheng, A. M. Elliot, J. Stafford, T. Olson, J. Z. Zhang, C. Li, *Mol. Cancer Ther.* 2008, 7, 1730.
[8] W. Lu, C. Xiong, G. Zhang, Q. Huang, R. Zhang, J. Z. Zhang, C. Li, *Clin. Cancer Res.* 2009, 15, 876.
[9] J. Zeng, Q. Zhang, J. Chen, Y. Xia, *Nano letters* 2010, 10, 30.
[10] X. Cao, Y. Ye, S. Liu, *Anal. Biochem.* 2011, 417, 1.
[11] K. Saha, S. S. Agasti, C. Kim, X. Li, V. M. Rotello, *Chem. Rev.* 2012, 112, 2739.
[12] H. Jans, Q. Huo, *Chem. Soc. Rev.* 2012, 41, 2849.
[13] J. Wang, A. Shi, X. Fang, X. Han, Y. Zhang, *Analytical biochemistry* 2015, 469, 71.
[14] X. Huang, Z. Xu, Y. Mao, Y. Ji, H. Xu, Y. Xiong, Y. Li, *Biosens. Bioelectron.* 2015, 66, 184.
[15] Y. Gong, X. Chen, Y. Lu, W. Yang, *Biosens. Bioelectron.* 2015, 66, 392.
[16] S. Preciado-Flores, D. A. Wheeler, T. M. Tran, Z. Tanaka, C. Jiang, M. Barboza-Flores, F. Qian, Y. Li, B. Chen, J. Z. Zhang, *Chem. Commun.* 2011, 47, 4129.
[17] A. J. Blanch, M. Doblinger, J. Rodriguez-Fernandez, *Small* 2015, 11, 4550.
[18] M. P. Melancon, M. Zhou, C. Li, *Acc. Chem. Res.* 2011, 44, 947.
[19] V. Shanmugam, S. Selvakumar, C.-S. Yeh, *Chem. Soc. Rev.* 2014, 43, 6254.
[20] K.-H. Chen, Y.-C. Pu, K.-D. Chang, Y.-F. Liang, C.-M. Liu, J.-W. Yeh, H.-C. Shih, Y.-J. Hsu, *J. Phys. Chem. C* 2012, 116, 19039.
[21] Q. Zhang, N. Large, P. Nordlander, H. Wang, *J. Phys. Chem. Lett.* 2014, 5, 370.
[22] X. Ye, L. Jin, H. Caglayan, J. Chen, G. Xing, C. Zheng, V. Doan-Nguyen, Y. Kang, N. Engheta, C. R. Kagan, C. B. Murray, *ACS Nano* 2012, 6, 2804.
[23] L. Vigderman, E. R. Zubarev, *Chem. Mater.* 2013, 25, 1450.
[24] S. E. Skrabalak, J. Chen, X. Lu, L. Au, C. M. Cobley, Y. Xia, *Acc. Chem. Res.* 2008, 41, 1587.
[25] Y. Xia, W. Li, C. M. Cobley, J. Chen, X. Xia, Q. Zhang, M. Yang, E. C. Cho, P. K. Brown, *Acc. Chem. Res.* 2011, 44, 914.
[26] S. N. Abdollahi, M. Naderi, G. Amoabediny, *Colloids Surf. A Physicochem. Eng. Asp.* 2013, 436, 1069.
[27] S. Adams, D. Thai, X. Mascona, A. M. Schwartzberg, J. Z. Zhang, *Chem. Mater.* 2014, 26, 6805.
[28] M. Prieto, R. Arenal, L. Henrard, L. Gomez, V. Sebastian, M. Arruebo, *J. Phys. Chem. C* 2014, 118, 28804.
[29] F. Hao, C. L. Nehl, J. H. Hafner, P. Nordlander, *Nano letters* 2007, 7, 729.
[30] Q. Zhang, Y. Hu, S. Guo, J. Goebl, Y. Yin, *Nano letters* 2010, 10, 5037.
[31] Z. Li, Y. Yu, Z. Chen, T. Liu, Z.-K. Zhou, J.-B. Han, J. Li, C. Jin, X. Wang, *J. Phys. Chem. C* 2013, 117,20127.
[32] A. M. Schwartzberg, T. Y. Olson, C. E. Talley, J. Z. Zhang, *J. Phys. Chem. B* 2006, 110, 19935.
[33] E. Hao, S. Li, R. C. Bailey, S. Zou, G. C. Schatz, J. T. Hupp, *J. Phys. Chem. B* 2004, 108, 1224.
[34] W. Lu, M. P. Melancon, C. Xiong, Q. Huang, A. Elliott, S. Song, R. Zhang, L. G. Flores, 2nd, J. G. Gelovani, L. V. Wang, G. Ku, R. J. Stafford, C. Li, *Cancer Res.* 2011, 71, 6116.
[35] N. Fairbairn, A. Christofidou, A. G. Kanaras, T. A. Newman, O. L. Muskens, *Phys. Chem. Chem. Phys.* 2013, 15, 4163.
[36] E. Carlson, G. Perez-Abadia, S. Adams, J. Z. Zhang, K. A. Kang, C. Maldonado, *Journal of Acupuncture and Meridian Studies* 2015.
[37] Y. Sun, B. Mayers, Y. Xia, *Adv. Mater.* 2003, 15, 641.
[38] D. A. Wheeler, R. J. Newhouse, H. Wang, S. Zou, J. Z. Zhang, *J. Phys. Chem. C* 2010, 114, 18126.
[39] T. Y. Olson, A. M. Schwartzberg, C. A. Orme, C. E. Talley, B. O'Connell, J. Z. Zhang, *J. Phys. Chem. C* 2008, 112, 6319.
[40] S. Preciado-Flores, D. Wang, D. A. Wheeler, R. J. Newhouse, J. K. Hensel, A. Schwartzberg, L. Wang, J. Zhu, M. Barboza-Flores, J. Z. Zhang, *J. Mater. Chem.* 2011, 21, 2344.
[41] V. Salgueirino-Maceira, M. A. Correa-Duarte, M. Farle, M. A. Lopez-Quintela, K. Sieradzki, R. Diaz, *Langmuir* 2006, 22, 1455.
[42] S. Adams, J. Z. Zhang, *Coord. Chem. Rev.* 2016, 320-321, 18.
[43] H.-P. Liang, L.-J. Wan, C.-L. Bai, L. Jiang, *J. Phys. Chem. B* 2005, 109, 7795.
[44] B. T. Draine, P. J. Flatau, *J. Opt. Soc. Am. A* 1994, 11, 1491.

[45] P. K. Jain, K. S. Lee, I. H. El-Sayed, M. A. El-Sayed, *J. Phys. Chem. B* 2006, 110, 7238.
[46] P. J. Flatau, B. T. Draine, *Opt. Express* 2014, 22, 21834.
[47] J. M. Sanz, D. Ortiz, R. Alcaraz de la Osa, J. M. Saiz, F. Gonzalez, A. S. Brown, M. Losurdo, H. O. Everitt, F. Moreno, *J. Phys. Chem. C* 2013, 19606-19615.
[48] P. B. Johnson, R. W. Christy, *Phys. Rev. B* 1972, 6, 4370.
[49] C. E. Roma'n-Vela'zquez, C. Noguez, J. Z. Zhang, *J. Phys. Chem. A* 2009, 113, 4068.
[50] A. B. Davila-Ibanez, J. L. Legido-Soto, J. Rivas, V. Salgueirino, *Phys. Chem. Chem. Phys.* 2011, 13, 20146.
[51] Y. Kobayashi, M. Horie, M. Konno, B. Rodriguez-Gonzalez, L. M. Liz-Marza, J. Phys. Chem. B 2003, 107, 7420.
[52] N. T. Thanh, N. Maclean, S. Mahiddine, *Chem. Rev.* 2014, 114, 7610.
[53] Y.-C. Pu, Y.-J. Hsu, *Nanoscale* 2014, 6, 3881.
[54] Y.-C. Pu, Y.-C. Chen, Y.-J. Hsu, *Appl. Catal. B: Environ.* 2010, 97, 389.
[55] Y.-C. Pu, G. Wang, K.-D. Chang, Y. Ling, Y. K. Lin, B. C. Fitzmorris, C.-M. Liu, X. Lu, Y. Tong, J. Z. Zhang, Y.-J. Hsu, Y. Li, *Nano letters* 2013, 13, 3817.
[56] Y.-C. Pu, W.-H. Lin, Y.-J. Hsu, *Appl. Catal. B: Environ.* 2015, 163, 343.
[57] M. A. Van Dijk, A. L. Tchebotareva, M. Orrit, M. Lippitz, S. Berciaud, D. Lasne, L. Cognet, B. Lounis, *Phys. Chem. Chem. Phys.* 2006, 8, 3486.
[58] J. Ye, P. V. Dorpe, W. V. Roy, K. Lodewijks, I. D. Vlaminck, G. Maes, G. Borghs, *J. Phys. Chem. C* 2009, 113, 3110.
[59] S. Kado, S. Yokomine, K. Kimura, *RSC Adv.* 2014, 4, 10830.
[60] D. D. Evanoff Jr, G. Chumanov, *J. Phys. Chem. B* 2004, 108, 13957.
[61] C. Langhammer, B. Kasemo, I. Zoric, J. Chem. Phys. 2007, 126, 194702.

Notwithstanding the appended claims, the disclosure is also defined by the following clauses:

1. A method of producing cobalt nanoparticles (Co NPs) of a pre-selected diameter, including:
combining:
a cobalt salt;
a capping agent; and
a reducing agent,
under Co NP synthesis conditions including a temperature selected to produce cobalt nanoparticles of a pre-selected diameter, where the temperature and pre-selected diameter are inversely related.
2. The method according to Clause 1, where the Co NP synthesis conditions include a constant temperature.
3. The method according to Clause 1, where the Co NP synthesis conditions include a temperature profile.
4. The method according to any one of Clauses 1 to 3, where the temperature is from about 5° C. to about 90° C.
5. The method according to Clause 4, where the temperature is from about 10° C. to about 80° C.
6. The method according to Clause 5, where the pre-selected diameter is from about 150 nm to about 30 nm.
7. The method according to any one of Clauses 1 to 6, where the cobalt salt is an anhydrous cobalt salt.
8. The method according to Clause 7, where the cobalt salt is $CoCl_2$.
9. The method according to any one of Clauses 1 to 8, where the capping agent is a sodium salt of citrate.
10. The method according to Clause 9, where the capping agent is trisodium citrate.
11. The method according to any one of Clauses 1 to 10, where the reducing agent is a salt including boron.
12. The method according to Clause 11, where the reducing agent includes a tetrahedral $BH_4^-$ anion.
13. The method according to Clause 12, where the reducing agent is $NaBH_4$.
14. The method according to any one of Clauses 1 to 13, further including producing cobalt nanoparticles of a different pre-selected diameter by combining:
a cobalt salt;
a capping agent; and
a reducing agent,
under Co NP synthesis conditions including a different temperature selected to produce cobalt nanoparticles of the different pre-selected diameter, where the different temperature and different pre-selected diameter are inversely related.
15. The method according to any one of Clauses 1 to 14, further including, subsequent to producing the cobalt nanoparticles, producing hollow gold nanospheres (HGNs) using the cobalt nanoparticles as scaffolds.
16. The method according to Clause 15, where the HGNs are produced via a galvanic exchange reaction.
17. The method according to Clause 15 or Clause 16, where the HGNs have a diameter of from about 10 to about 200 nm.
18. The method according to any one of Clauses 15 to 17, where the HGNs exhibit a surface plasmon resonance (SPR) absorption with a maximum peak position of from about 565 to about 850 nm.
19. The method according to any one of Clauses 15 to 18, further including, subsequent to producing the HGNs, attaching a targeting moiety to the surface thereof.
20. The method according to Clause 19, where the targeting moiety is selected from the group consisting of: an antibody, a ligand, an aptamer, a nucleic acid, and a small molecule.
21. The method according to Clause 19 or Clause 20, where the targeting moiety binds to a molecule on the surface of a target cell.
22. The method according to Clause 21, where the target cell is a cancer cell.
23. Cobalt nanoparticles produced according to the method of any one of Clauses 1 to 13.
24. Hollow gold nanospheres (HGNs) produced according to the method of any one of Clauses 15 to 22.
25. A pharmaceutical composition, including:
the hollow gold nanospheres (HGNs) of Clause 24; and
a pharmaceutically acceptable carrier.
26. A kit, including:
the cobalt nanoparticles of Clause 23; and
instructions for using the cobalt nanoparticles to produce hollow gold nanospheres (HGNs).
27. The kit of Clause 26, further including one or more reagents for producing HGNs from the cobalt nanoparticles.
28. The kit of Clause 26 or Clause 27, where the instructions are for using the cobalt nanoparticles to produce HGNs via a galvanic exchange reaction.
29. A kit, including:
the hollow gold nanospheres (HGNs) of Clause 24; and
instructions for using the HGNs to detect an analyte in vitro or in vivo.
30. A kit, including:
the hollow gold nanospheres (HGNs) of Clause 24 or the pharmaceutical composition of Clause 25; and
instructions for administering the HGNs to an individual in need thereof.

31. The kit of Clause 30, where the HGNs include a targeting moiety that binds to a molecule on the surface of a target cell of the individual.
32. The kit of Clause 31, where the target cell is a cancer cell.
33. A method including administering the hollow gold nanospheres (HGNs) of Clause 24 or the pharmaceutical composition of Clause 25 to an individual in need thereof.
34. The method according to Clause 33, where the HGNs include a targeting moiety that binds to a molecule on the surface of a target cell of the individual.
35. The method according to Clause 34, where the target cell is a cancer cell.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of producing cobalt nanoparticles (Co NPs) of a pre-selected diameter, comprising:
   (a) pre-selecting a desired diameter of Co NPs prior to production of the Co NPs;
   (b) selecting a temperature of from 10° C. to 80° C. for Co NP synthesis for achieving the pre-selected desired diameter of the Co NPs;
   (c) selecting:
      a cobalt salt;
      a capping agent; and
      a reducing agent,
   capable of forming Co NPs under Co NP synthesis conditions, wherein said Co NP synthesis conditions include an inverse relationship between a temperature of synthesis and a resulting diameter of Co NPs produced over the entire range of from 10° C. to 80° C., and
   d) combining the cobalt salt, capping agent and reducing agent at the selected temperature to produce Co NPs of the desired diameter.

2. The method according to claim 1, wherein the Co NP synthesis conditions comprise a constant temperature.

3. The method according to claim 1, wherein the pre-selected diameter is from about 150 nm to about 30 nm.

4. The method according to claim 1, wherein the cobalt salt is $CoCl_2$.

5. The method according to claim 1, wherein the capping agent is trisodium citrate.

6. The method according to claim 1, wherein the reducing agent is $NaBH_4$.

7. The method according to claim 1, further comprising producing cobalt nanoparticles of a different pre-selected diameter by:
   (d) pre-selecting a different desired diameter of Co NPs prior to production of the Co NPs;
   (e) selecting a different temperature of from 10° C. to 80° C. for the Co NP synthesis for achieving the different pre-selected desired diameter of the Co NPs; and
   (f) combining the
      cobalt salt
      capping agent and
      reducing agent
      under Co NP synthesis conditions comprising the different temperature to produce Co NPs of the different pre-selected diameter.

8. The method according to claim 1, further comprising, subsequent to producing the cobalt nanoparticles, producing hollow gold nanospheres (HGNs) using the cobalt nanoparticles as scaffolds.

9. The method according to claim 8, wherein the HGNs are produced via a galvanic exchange reaction.

10. The method according to claim 8, wherein the HGNs have a diameter of from about 10 to about 200 nm.

11. The method according to claim 8, wherein the HGNs exhibit a surface plasmon resonance (SPR) absorption with a maximum peak position of from about 565 to about 850 nm.

12. The method according to claim 8, further comprising, subsequent to producing the HGNs, attaching a targeting moiety to the surface thereof.

* * * * *